US012239227B2

(12) United States Patent
Richardson et al.

(10) Patent No.: US 12,239,227 B2
(45) Date of Patent: *Mar. 4, 2025

(54) STOOLS, CHAIRS, AND METHODS USING THE SAME

(71) Applicant: InkBed, Inc., Mukilteo, WA (US)

(72) Inventors: Kevin Richardson, Everett, WA (US); Edgar Zavala, Mukilteo, WA (US)

(73) Assignee: INKBED, INC., Mukilteo, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/475,066

(22) Filed: Sep. 26, 2023

(65) Prior Publication Data

US 2024/0130530 A1 Apr. 25, 2024
US 2024/0225284 A9 Jul. 11, 2024

Related U.S. Application Data

(63) Continuation of application No. 17/175,539, filed on Feb. 12, 2021, now Pat. No. 11,805,904, which is a
(Continued)

(51) Int. Cl.
*A47C 1/00* (2006.01)
*A47C 3/00* (2006.01)
(Continued)

(52) U.S. Cl.
CPC .................. *A47C 1/00* (2013.01); *A47C 3/00* (2013.01); *A47C 7/00* (2013.01); *A47C 7/004* (2013.01);
(Continued)

(58) Field of Classification Search
CPC .. A47C 7/54; A47C 7/00; A47C 7/006; A47C 7/543; A47C 9/00; A47C 9/002;
(Continued)

(56) References Cited

U.S. PATENT DOCUMENTS 3,188,136 A 6/1965 Redfield et al.
3,227,440 A 1/1966 Scott
(Continued)

FOREIGN PATENT DOCUMENTS

CN 2151738 Y 1/1994
CN 201119969 Y 9/2008
(Continued)

OTHER PUBLICATIONS

"Hydraulic All Purpose Tattoo Chair KI New York", http://www.puretat.com, accessed Jan. 18, 2010, 2 pages.
(Continued)

*Primary Examiner* — Chi Q Nguyen
(74) *Attorney, Agent, or Firm* — Perkins Coie LLP

(57) ABSTRACT

An apparatus that supports a user in a variety of positions to comfortably perform tasks, such as applying one or more tattoos to skin of a subject is herein disclosed. The apparatus can be reconfigured to optimally position and support the arms and/or chest of the user. A method for using a stool can involve rotating armrests of the apparatus from a stowed position to a deployed position. The armrests can support the user's forearms while supporting the user's chest such that the user can comfortably perform tasks in front of a chest support of the stool.

10 Claims, 21 Drawing Sheets

Related U.S. Application Data continuation of application No. 16/731,820, filed on Dec. 31, 2019, now Pat. No. 10,959,523, which is a continuation of application No. 16/363,862, filed on Mar. 25, 2019, now Pat. No. 10,524,573, which is a continuation-in-part of application No. 15/811,127, filed on Nov. 13, 2017, now Pat. No. 10,238,213, which is a continuation of application No. 15/248,824, filed on Aug. 26, 2016, now Pat. No. 9,814,313, which is a continuation of application No. 14/791,110, filed on Jul. 5, 2015, now Pat. No. 9,451,831, which is a continuation of application No. 14/151,753, filed on Jan. 9, 2014, now Pat. No. 9,084,486, said application No. 16/363,862 is a continuation of application No. 15/121,754, filed as application No. PCT/US2015/010910 on Jan. 9, 2015, now Pat. No. 10,506,881, and a continuation-in-part of application No. 14/151,753, filed on Jan. 9, 2014, now Pat. No. 9,084,486.

(60) Provisional application No. 62/048,184, filed on Sep. 9, 2014.

(51) Int. Cl.
| | |
|---|---|
| *A47C 7/00* | (2006.01) |
| *A47C 7/54* | (2006.01) |
| *A47C 9/00* | (2006.01) |
| *A47C 9/02* | (2006.01) |
| *A47C 13/00* | (2006.01) |
| *A47C 15/00* | (2006.01) |
| *A61G 15/00* | (2006.01) |
| *A61G 15/12* | (2006.01) |
| *A61M 37/00* | (2006.01) |
| *A47C 1/11* | (2006.01) |
| *A61B 90/60* | (2016.01) |
| *A61G 13/12* | (2006.01) |

(52) U.S. Cl.
CPC ............... *A47C 7/006* (2013.01); *A47C 7/54* (2013.01); *A47C 7/543* (2013.01); *A47C 9/00* (2013.01); *A47C 9/002* (2013.01); *A47C 9/02* (2013.01); *A47C 13/00* (2013.01); *A47C 15/004* (2013.01); *A61G 15/007* (2013.01); *A61G 15/12* (2013.01); *A61M 37/0076* (2013.01); *A47C 1/11* (2013.01); *A47C 9/005* (2013.01); *A61B 90/60* (2016.02); *A61G 13/122* (2013.01); *A61G 13/1235* (2013.01)

(58) Field of Classification Search
CPC ......... A47C 13/00; A47C 1/11; A47C 15/004; A47C 9/005; A47C 9/02; A61G 15/007; A61G 15/12; A61G 13/122; A61G 13/1235; A61B 19/28; A61B 90/60; A61M 37/0076

See application file for complete search history.

(56) References Cited

U.S. PATENT DOCUMENTS

| | | | |
|---|---|---|---|
| 3,319,747 | A | 5/1967 | Lauper |
| 4,159,145 | A | 6/1979 | Quakenbush |
| 4,170,800 | A | 6/1979 | Quakenbush |
| 4,285,541 | A | 8/1981 | Onishi |
| 4,387,888 | A | 6/1983 | Marinakis |
| 4,516,805 | A | 5/1985 | Leeper et al. |
| 4,650,249 | A | 3/1987 | Serber |
| 4,660,549 | A | 3/1987 | Serber |
| 4,795,214 | A | 1/1989 | Holdt |
| 4,832,407 | A | 1/1989 | Holdt |
| 5,060,327 | A | 10/1991 | Celestina et al. |
| 5,086,769 | A | 2/1992 | Vianello et al. |
| 5,098,158 | A | 2/1992 | Vianello et al. |
| 5,315,722 | A | 5/1994 | Djie |
| 5,401,078 | A | 3/1995 | Riach |
| 5,487,590 | A | 1/1996 | Haynes |
| 5,642,542 | A | 7/1997 | Kometani |
| 5,645,313 | A | 7/1997 | Kometani |
| 5,653,499 | A | 7/1997 | Best et al. |
| 5,678,894 | A | 8/1997 | Goodall |
| 5,762,402 | A | 6/1998 | Gillotti |
| 5,967,610 | A | 10/1999 | Lin |
| 5,971,475 | A | 10/1999 | Lin |
| 5,971,485 | A | 10/1999 | Lawson et al. |
| 6,003,940 | A * | 12/1999 | Jackson ................. A47C 7/543 297/217.3 |
| 6,089,593 | A | 7/2000 | Hanson et al. |
| 6,135,548 | A | 7/2000 | Hanson et al. |
| 6,212,713 | B1 | 4/2001 | Kuck et al. |
| 6,315,319 | B1 | 4/2001 | Kuck et al. |
| 6,446,287 | B2 | 9/2002 | Borders |
| 6,543,853 | B1 | 4/2003 | Splane, Jr. |
| 6,619,747 | B2 | 4/2003 | Splane, Jr. |
| 6,767,066 | B1 | 7/2004 | Tornero |
| 6,824,219 | B2 | 7/2004 | Tornero |
| 6,846,042 | B2 | 1/2005 | Hanson et al. |
| 6,918,143 | B2 | 1/2005 | Hanson et al. |
| 7,021,037 | B1 | 4/2006 | Szymas |
| 7,080,885 | B2 | 4/2006 | Szymas |
| 7,234,768 | B2 | 6/2007 | Manning |
| 7,293,834 | B2 | 6/2007 | Manning et al. |
| 7,357,456 | B1 | 4/2008 | Freer et al. |
| 7,600,817 | B2 | 10/2009 | Kramer et al. |
| 7,784,871 | B2 | 8/2010 | Cochran |
| 8,651,569 | B2 | 2/2014 | Andoloro et al. |
| 9,084,486 | B1 | 7/2015 | Richardson et al. |
| 9,375,088 | B2 | 6/2016 | Andoloro |
| 9,451,831 | B2 | 6/2016 | Andoloro |
| 9,498,398 | B1 | 9/2016 | Richardson et al. |
| 9,814,313 | B2 | 11/2017 | Richardson et al. |
| 9,853,438 | B2 | 11/2017 | Richardson et al. |
| 10,238,213 | B2 | 3/2019 | Richardson et al. |
| 10,264,885 | B2 | 4/2019 | Andoloro et al. |
| 10,383,444 | B1 | 8/2019 | Parkins |
| 10,506,881 | B2 | 12/2019 | Richardson et al. |
| 10,517,404 | B2 | 12/2019 | Hopper et al. |
| 10,524,573 | B2 | 1/2020 | Richardson et al. |
| 10,638,843 | B2 | 1/2020 | Richardson et al. |
| 10,918,213 | B2 | 2/2021 | Fryer |
| 10,959,523 | B2 | 2/2021 | Fryer |
| 10,973,725 | B2 | 3/2021 | Richardson et al. |
| 11,564,495 | B1 * | 1/2023 | Arnett ................. A47C 1/022 |
| 11,707,136 | B2 * | 7/2023 | Richardson ............ A47C 7/541 297/411.36 |
| 11,805,904 | B2 | 7/2023 | Richardson et al. |
| 11,730,269 | B1 * | 8/2023 | Rosebrook ........... A47C 7/5064 297/423.12 |
| 11,850,105 | B2 * | 12/2023 | Bruni ..................... A47C 7/029 |
| 2002/0000008 | A1 | 1/2002 | Borders |
| 2002/0067060 | A1 | 6/2002 | Lloyd |
| 2002/0158492 | A1 | 10/2002 | Ko et al. |
| 2004/0133979 | A1 | 7/2004 | Newkirk et al. |
| 2005/0104435 | A1 | 5/2005 | Bain et al. |
| 2006/0225212 | A1 | 10/2006 | Parson et al. |
| 2007/0035164 | A1 | 2/2007 | North |
| 2007/0052275 | A1 | 3/2007 | Ghilzai |
| 2007/0108805 | A1 | 5/2007 | Manning |
| 2009/0250565 | A1 | 10/2009 | Jaggers et al. |
| 2009/0295213 | A1 | 12/2009 | White |
| 2010/0295357 | A1 | 11/2010 | Koehler et al. |
| 2011/0272976 | A1 | 11/2011 | Wei et al. |
| 2016/0157618 | A1 | 6/2016 | Arnett |
| 2017/0013960 | A1 * | 1/2017 | Richardson ............ A61B 90/60 |

(56) References Cited

U.S. PATENT DOCUMENTS

2018/0255932 A1 9/2018 Hopper
2024/0081541 A1 3/2024 Richardson

FOREIGN PATENT DOCUMENTS

| JP | 5284532 B1 | 9/2013 |
|----|------------|--------|
| WO | 2009056004 A1 | 5/2009 |
| WO | 2011087232 A2 | 7/2011 |
| WO | 2013078569 A1 | 6/2013 |

OTHER PUBLICATIONS

"Tatsoul 370" http://www.tatsoul.com, accessed Feb. 2, 2010, 7 pages.
"Tattoo-Chairs-table", http://www.tattoochair.com, © 2009, accessed Jan. 18, 2010, 7 pages.
"Traveler—The Ultimate Table", http://www.tattootable.com, Fab Tech, accessed Jan. 18, 2010, 3 pages.
Extended European Search Report for European Application No. 15735366.5; Date of Mailing; Jul. 6, 2017; 7 pages.
First Examination Report mailed Sep. 12, 2018 in Australian Patent Application No. 2015204573, 4 pages.
International Search Report and Written Opinion mailed Jun. 3, 2019 in International Patent Application No. PCT/US19/18100, 15 pages.
International Searching Authority, International Search Report and Written Opinion, PCT Patent Application PCT/US2015/010910, mailed May 11, 2015, 14 pages.
Office Action mailed Apr. 26, 2019 in Chinese Patent Application No. 201580003983.7, with English Translation, 21 pages.
Office Action mailed Feb. 17, 2021 in Canada Patent Application No. 2,935,140, 3 pages.
Office Action mailed Jun. 4, 2020 in Chinese Patent Application No. 201580003983.7, with English Translation, 21 pages.
Office Action mailed Dec. 8, 2023 in Chinese Patent Application No. 202110098185.4, with English Translation, 22 pages.
Office Action mailed May 18, 2022 in Canada Patent Application No. 2,935,140, 6 pages.
Office Action mailed Sep. 24, 2021 in Canada Patent Application No. 2,935,140, 4 pages.
Office Action mailed Sep. 30, 2019 in Chinese Patent Application No. 201580003983.7, with English Translation, 8 pages.
Office Action mailed Sep. 6, 2018 in Chinese Patent Application No. 201580003983.7, with English Translation, 21 pages.
Tatsoulsupply. TATSoul Artist Chair Review—YouTube. YouTube, Mar. 20, 2013. [Retrieved Mar. 13, 2015]. Retrieved from Internet <URL: https://www.youtube.com/watch?v=JBNqVAItTQw>.

* cited by examiner

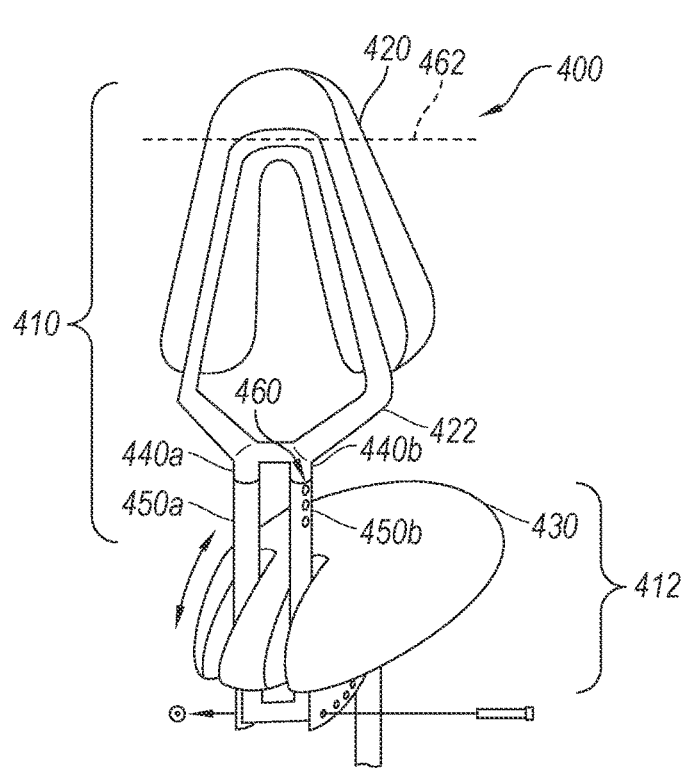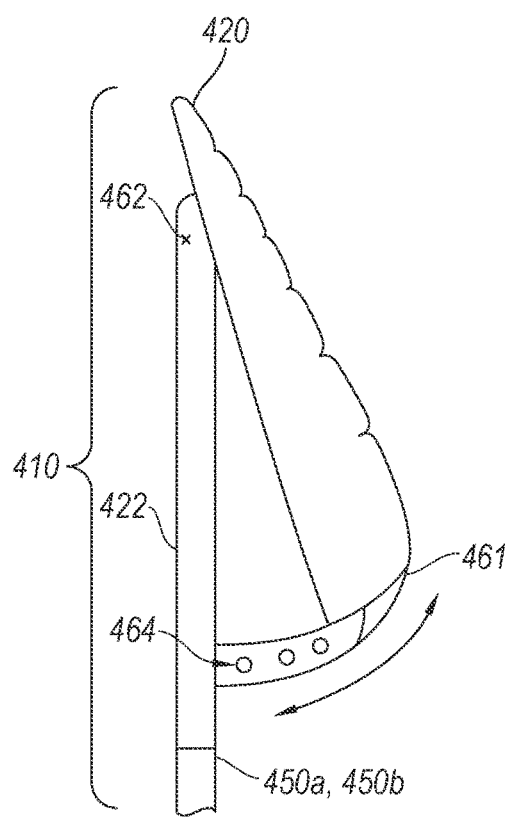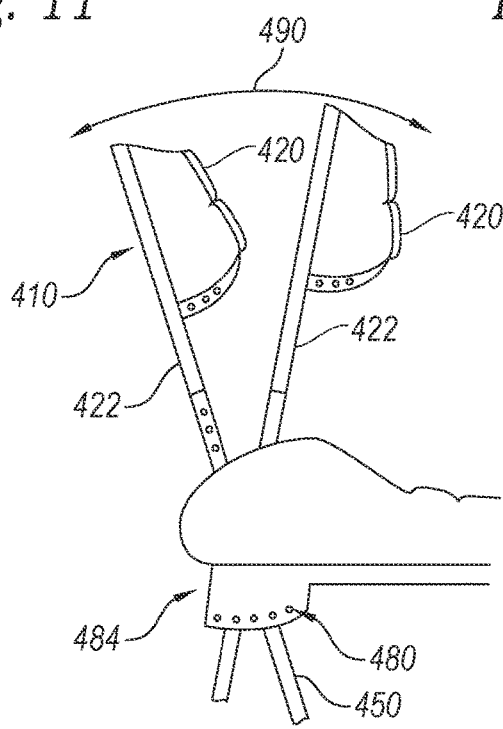
Fig. 11
Fig. 12
Fig. 13

STOOLS, CHAIRS, AND METHODS USING THE SAME

CROSS-REFERENCE TO RELATED APPLICATIONS

This application is a continuation of U.S. patent application Ser. No. 17/175,539, filed Feb. 12, 2021, entitled "STOOLS, CHAIRS, AND METHODS USING THE SAME," (now U.S. Pat. No. 11,805,904), which is a continuation of U.S. patent application Ser. No. 16/731,820, filed Dec. 31, 2019 (now U.S. Pat. No. 10,959,523), entitled "STOOLS, CHAIRS, AND METHODS USING THE SAME," which is a continuation of U.S. patent application Ser. No. 16/363,862, filed Mar. 25, 2019 (now U.S. Pat. No. 10,524,573), entitled "STOOLS, CHAIRS, AND METHODS USING THE SAME," which is a continuation of U.S. patent application Ser. No. 15/121,754, filed Aug. 25, 2016 (now U.S. Pat. No. 10,506,881), entitled "STOOLS, CHAIRS, AND METHODS USING THE SAME," which is a national phase application of PCT/US15/10910, filed Jan. 9, 2015, entitled "STOOLS, CHAIRS, AND METHODS USING THE SAME," which claims the benefit of U.S. App. No. 62/048,184, filed Sep. 9, 2014, entitled "STOOLS AND CHAIRS AND METHODS USING THE SAME," and is a continuation-in-part of U.S. patent application Ser. No. 14/151,753, filed Jan. 9, 2014 (now U.S. Pat. No. 9,084,486), entitled "TATTOO STOOLS AND CHAIRS AND METHODS USING THE SAME." U.S. patent application Ser. No. 16/363,862 is also a continuation-in-part of U.S. patent application Ser. No. 15/811,127, filed Nov. 13, 2017 (now U.S. Pat. No. 10,238,213), entitled "STOOLS, CHAIRS, AND METHODS USING THE SAME," which is a continuation of U.S. patent application Ser. No. 15/248,824, filed Aug. 26, 2016 (now U.S. Pat. No. 9,814,313), entitled "STOOLS, CHAIRS, AND METHODS USING THE SAME," which is a continuation of U.S. patent application Ser. No. 14/791,110, filed Jul. 2, 2015 (now U.S. Pat. No. 9,451,831), entitled "STOOLS, CHAIRS AND METHODS USING THE SAME," which is a continuation of U.S. patent application Ser. No. 14/151,753, filed Jan. 9, 2014 (now U.S. Pat. No. 9,084,486) entitled "TATTOO STOOLS AND CHAIRS AND METHODS USING THE SAME." All of these applications and patents are incorporated by reference herein in their entireties.

TECHNICAL FIELD

The present technology is related to support apparatuses and associated methods of using the same. In particular, the present technology is related to reconfigurable stools and chairs.

BACKGROUND

Conventional stools and chairs are not designed to support an occupant's chest and arms when the occupant leans forward. In tattoo parlors, tattoo artists often sit on stools or chairs while applying tattoos. Unfortunately, conventional stools and chairs are not ergonomically designed for tattoo artists and are not comfortable when, for example, leaning forward and applying tattoos. For example, a tattoo artist's arms and shoulders can experience significant fatigue when applying large intricate tattoos. Additionally, when a tattoo artist leans forward for a significant period of time, the artist's lower back may experience fatigue and discomfort. In medical environments, physicians, nurses, or other medical personnel frequently sit and lean forward to perform tasks, which may cause lower back pain. Accordingly, there is a need for stools or chairs that comfortably support an occupant's body without hindering movement of the occupant's shoulders, arms, hands, or other body parts.

SUMMARY OF TECHNOLOGY

An exemplary embodiment is a support apparatus for supporting a user. The support apparatus can place the user's body in ergonomic positions to help reduce or limit fatigue (e.g., muscle fatigue in the user's arms, shoulders, back, etc.), discomfort, and/or pain. The user can straddle the apparatus and can lean forward against a padded chest support. The padded chest support can be narrower than the user's chest and/or shoulders to provide unrestricted movement of the user's arms on the front side of the chest support. The support apparatus can have armrests that are shorter than the user's forearms to provide unrestricted movement of the user's wrists and/or hands while the user's forearms rest on the armrests. The user can sit in different directions on the support apparatus. When sitting facing the chest support, the user can lean forward against the chest support. When facing the opposite direction, the chest support can function as a back support, and the armrests can be stowed to help support the sides of the user's back.

The support apparatus can be a stool, a chair, or other reconfigurable equipment capable of supporting the user's body in ergonomic positions. In tattoo parlors, the support apparatus can place a tattoo artist's body in different ergonomic positions to help eliminate, reduce, or limit fatigue associated with tattooing. The support apparatus can also be used by a client (i.e., a person obtaining a tattoo). In one embodiment, a tattooing stool can support a tattoo artist in a variety of positions to comfortably apply one or more tattoos to skin of a client. The apparatus can be reconfigured to optimally position and support the arm (s) and/or chest of the tattoo artist. A method for using a tattoo stool can involve rotating armrests between a stowed position for supporting the tattoos artist's chest and/or shoulders to a deployed position for supporting the tattoo artist's arms. For example, armrests can support the user's forearms while a chest support supports the user's chest such that the artist can comfortably tattoo a body part of the subject positioned in front of the tattoo stool. In medical settings, a doctor, a nurse, lab technician, or other medical personnel can use the support apparatus to perform tasks, such as laboratory work, blood drawing, etc. The support apparatus can also be used in massage parlors, salons, spas, or other desired locations.

In some embodiments, a stool comprises a seat assembly and a chest support assembly. The chest support assembly can include a padded support and at least one armrest moveable between a stowed position and a deployed position. The padded support is configured to support the chest of a user (e.g., a tattoo artist) sitting on the seat assembly while allowing the user's arms to move freely on a front side of the padded support. The armrest, in the deployed position, can extend away from the padded support such that the user's arm is capable of resting on the portion of the armrest located in front of the padded support. The user can adjust the configuration of the stool any number of times during use (e.g., a tattoo session). The seat assembly, in some embodiments, includes a seat, a pedestal, hydraulics, mechanisms (e.g., locking mechanisms, tilt adjustment mechanisms, etc.), and/or a plurality of wheels for rolling along a support surface. When straddling the stool (e.g., a user straddles a vertical support of the chest assembly), the user can conveniently wheel the stool along the support surface. The seat assembly can include a swiveling padded seat to permit convenient rotation. In the stowed position, the armrest can be positioned alongside the padded support. In the deployed position, an elongated main body of the armrest can extend substantially perpendicular to the padded support. The armrest can also be located at other orientations.

In some embodiments, a support apparatus comprises a seat assembly, a chest support, and an armrest. The chest support can be carried by the seat assembly and is positioned to contact the front of the user's chest while the user sits on the seat assembly. An end of the armrest can move away from the user's chest when the armrest rotates from a raised position to a lowered position. In the raised position, the armrest can support the user's chest and/or shoulders for enhanced comfort. In the fully lowered position, the armrest can be positioned to support a user's forearm. For example, the lowered armrest can be oriented generally horizontally. The end of the lowered armrest and seat assembly can be positioned on opposite sides of a chest pad of the chest support. In some embodiments, most of the length of the armrest (e.g., 70%, 80%, 90%, or 95% of the total length of the armrest) and most of the seat are located on opposite sides of an imaginary vertical plane (e.g., a vertical plane positioned along the chest support).

The support apparatus, in some embodiments, can include a pair of armrests rotatably coupled to opposing sides of the chest support. The armrests rotate together or independently relative to the chest support. For example, a pivoting mechanism can rotatably couple one armrest to the left side of the chest support, and another pivoting mechanism can rotatably couple the other armrest to the right side of the chest support. The pivoting mechanisms can have different states of operation, such as a locked state and an unlocked state. In one embodiment, the pivoting mechanisms can be biased toward the locked state.

In further embodiments, a support apparatus can comprise a seat assembly, means for supporting a user's chest, and means for supporting the user's arm. The seat assembly can carry the means for supporting the chest of the user. The means for supporting the user's arm can support a user's arm while the user sits on the seat assembly and the user's chest rests against the means for supporting the user's chest. In one embodiment, the means for supporting the user's chest includes a padded chest support and a vertical rod, which couples the padded chest support to the seat assembly. The means for supporting the user's arm can include one or more rotatable armrests, which can be padded for enhanced comfort.

In yet further embodiments, a method for using a stool or a chair is provided. The method comprises rotating at least one armrest of the stool or chair from a stowed position to a lowered position. In one embodiment, a tattoo artist can tattoo at least a portion of a subject (e.g., a client) while the lowered armrest supports the artist's arm and also while the artist's chest rests against a chest support of the stool. The artist can comfortably lean against the chest support, which is movable between vertical and inclined positions. Alternatively, the client can sit on the stool, and the client's arm can rest on the armrest while it is tattooed. The method can also be performed using a chair that includes a chest support and armrests.

BRIEF DESCRIPTION OF THE DRAWINGS

FIG. 11 is an isometric view of a chest support assembly in accordance with an embodiment of the present technology.

FIG. 12 is a side view of the chest support assembly of FIG. 11 with a tilted chest support.

FIG. 13 is a side view of the chest support assembly of FIG. 11 in different positions.

DETAILED DESCRIPTION

Figure 2:
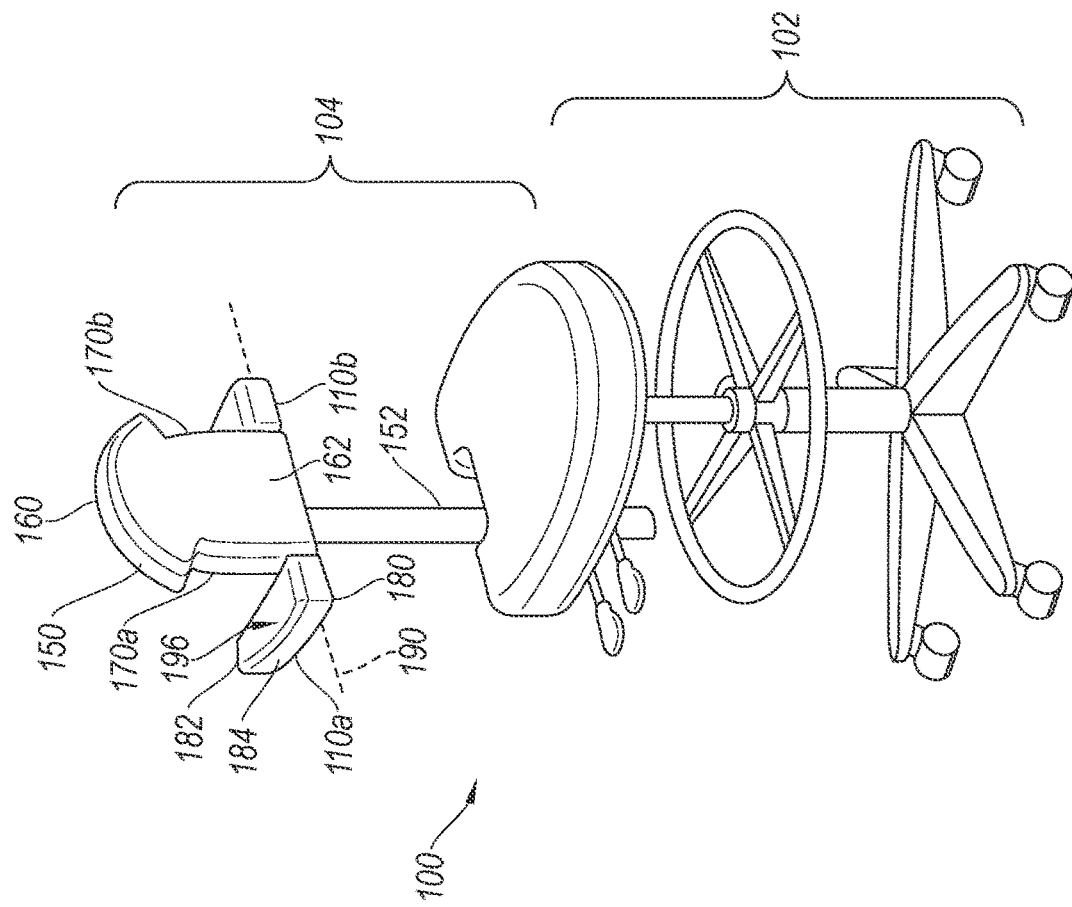
FIG. 2 is an isometric view of the stool of FIG. 1 with lowered armrests.
Figure 1:
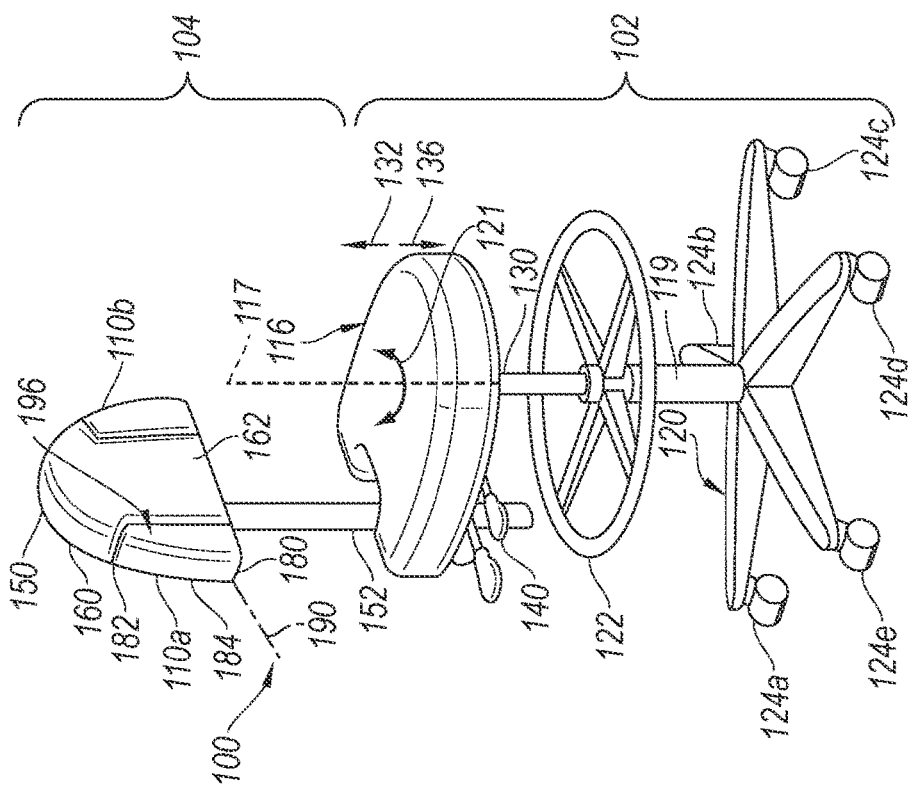
FIG. 1 is an isometric view of a stool with raised armrests in accordance with an embodiment of the present technology.

FIG. 1 is an isometric view of a stool 100 in accordance with an embodiment of the present technology. The stool 100 can include a seat assembly 102 and a chest support assembly 104. A user can sit on the seat assembly 102 such that the user's chest rests against the chest support assembly 104. The chest support assembly 104 can help position the user's upper body and can include armrests 110a, 110b (collectively "armrests 110") movable between stowed or raised positions (FIG. 1) and lowered or deployed positions (FIG. 2). The raised armrests 110 of FIG. 1 are positioned to contact and support the user's chest whereas the lowered armrests 110 of FIG. 2 can support the user's forearms. The armrests 110 can be raised and lowered any number of times to position the user's arms at different locations. If the user is a tattoo artist ("artist"), the armrests 110 can be moved to different positions to tattoo different parts of a person's body.

FIG. 1 shows the seat assembly 102 including a seat 116 and a base assembly 120. The seat 116 can be padded for comfortable sitting. The base assembly 120 can include a base member 119, a foot rest 122, and wheels 124a, 124b, 124c, 124d, 124e (collectively "wheels 124"). The base member 119 can include a hydraulic assembly 130 used to raise (indicated by arrow 132) and lower (indicated by arrow 136) the seat 116. The hydraulic assembly 130 can include a bearing mount or pivot that allows rotation (indicated by arrow 121) of the seat 116 about a vertical axis of rotation 117. A control element in the form of a lever 140 can be used to lower the seat 116. The foot rest 122 can be a ring fixedly coupled to the hydraulic assembly 130 or other component of the base member 119. The wheels 126 can be casters configured to roll along a support surface. The base assembly 120 can have other configurations that provide desired functionality.

Referring to FIG. 2, chest support assembly 104 can include a chest support 150 and an elongate member 152. The chest support 150 has a front side 160 facing away from an occupant and a backside 162 facing the occupant during use. The chest support 150 can include armrest-receiving portions 170a, 170b having complementary shapes with the armrests 110a, 110b, respectively. When the armrests 110 are in the stowed position (FIG. 1), the armrests 110a, 110b can be received by the armrest-receiving portions 170a, 170b, respectively, such that the chest support assembly 104 (i.e., the chest support 150 and armrests 110) has an upside down U-shape configuration or partially elliptical configuration. The size and configuration of the chest support assembly 104 can be selected based on the desired amount of cushion, size of the user, and/or desired range of motion of the user.

The armrests 110a, 110b can be generally similar to each other, and accordingly, the description of one armrest 110a, 110b applies equal to the other armrest 110a, 110b, unless indicated otherwise. The armrest 110a can include a mounting end 180, a terminal end 182, and an elongated main body 184 therebetween. The mounting end 180 can be pivotally coupled to the chest support 150. The elongated main body 184 can have an upper surface 196 upon which the user's arm can rest. A rod (not shown) within the chest support 150 can couple the armrests 110a, 110b together. As such, the armrests 110 can rotate together about an axis of rotation 190. In other embodiments, the armrests 110 are independently rotatable about the axis of rotation 190. For example, one armrest 110 can be in the stowed position while the other armrest 110 can be in the deployed position. The axis of rotation 190 can be a horizontally oriented axis for up and down rotation of the armrests 110, but the axis of rotation 190 can be other orientations.

Figures 3, 4:
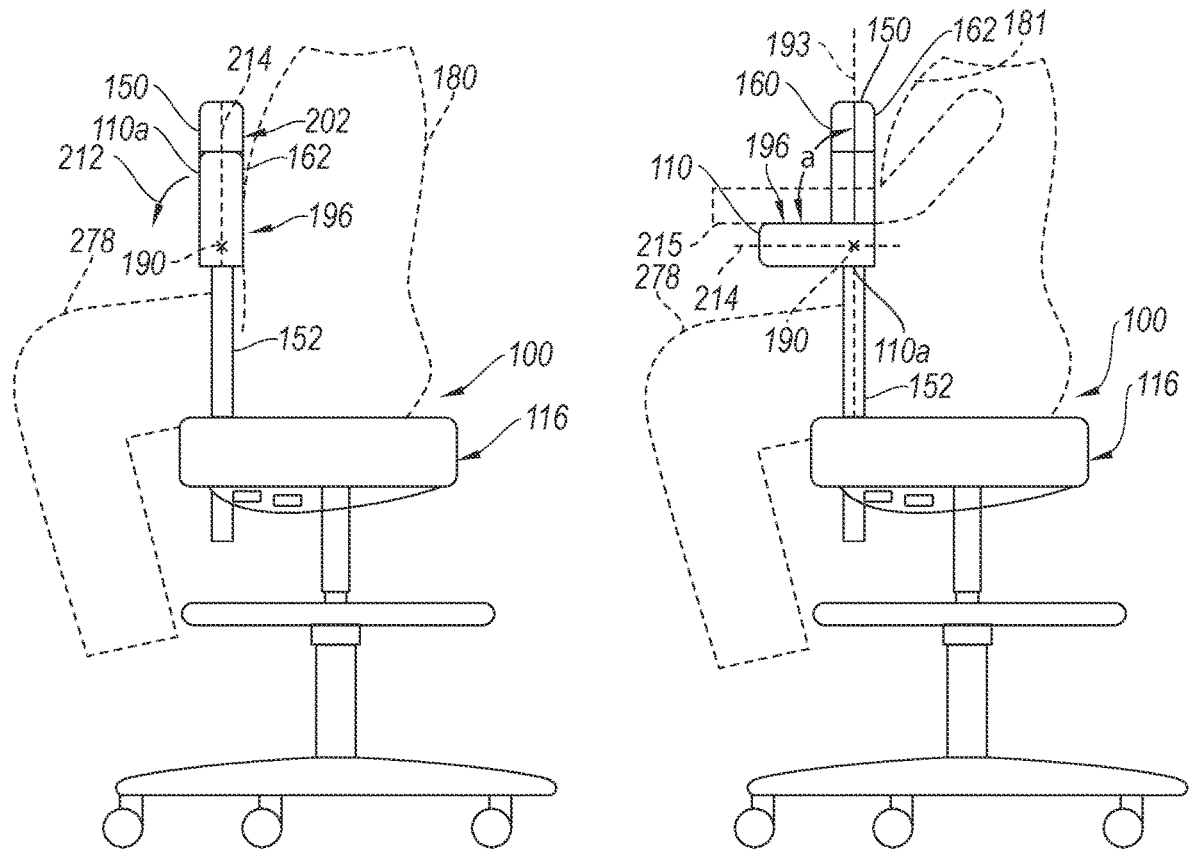
FIG. 3 is a side view of the stool of FIG. 1 with raised armrests and a user sitting on the stool.
FIG. 4 is a side view of the stool of FIG. 1 with lowered armrests and the user sitting on the stool.

FIG. 3 is a side view of the stool 100 with raised armrests 110. FIG. 4 is a side view of the stool 100 with lowered armrests 110. Referring now to FIG. 3, the stowed armrests 110 can be at an upright or substantially vertical orientation. As used herein, the term "substantially vertical" includes ranges of small angles from vertical, for example, angles between about 0 degrees and 10 degrees from vertical, such as angles less than about 5 degrees, for example, angles less than about 3 degrees, 2.5 degrees, or 2 degrees. The upper surface 196 can be approximately flush with a surface 202 of the chest support 150, illustrated in a substantially vertical orientation. The chest support 150 and the armrests 110 provide a relatively large surface area for contacting the user's chest and/or shoulders.

Referring to FIGS. 3 and 4, the armrest 110 can rotate (indicated by arrow 212 in FIG. 3) about the axis of rotation 190 an angle α (FIG. 4). In some embodiments, the angle α (FIG. 4) can be about 70 degrees to about 100 degrees. In one embodiment, the armrest 110a is rotatable along an arc of about 80 degrees to about 90 degrees. In one embodiment, the angle α is about 90 degrees. The armrest 110 can be rotated from an upright position in which a longitudinal axis 214 of the armrest 110a is substantially vertical (FIG. 3) to the fully deployed position in which the longitudinal axis 214 is substantially horizontal (FIG. 4). As used herein, the term "substantially horizontal" includes ranges of small angles from horizontal, for example, angles between about 0 degree and 10 degrees from horizontal, such as angles less than about 5 degrees, for example, angles less than about 2.5 degrees. In other embodiments, the fully lowered armrest 110 can be located at other orientations, such as a declined orientation, selected based on the desired body position of the user.

Referring to FIG. 4, the armrest 110 can extend substantially perpendicular to the vertically oriented chest support 150 and away from the user's torso during use. The user's chest 181 (illustrated in phantom line) can contact the backside 162 of the chest support 150, and the user's arm 215 can rest on the armrest 110, which extends outwardly on the front side 160 of the chest support 150. As such, the armrests 110 and seat 116 extend away from opposite sides of a coronal plane 193 of the chest support 150. The armrest 110 can be shorter than the user's forearm to provide unrestricted movement of the user's wrist and/or hand. In some embodiments, the length of the armrest 110 is in a range of about 5 inches (12.7 cm) to about 1 ft. (30.5 cm), but other lengths can be selected based on, for example, the length of the user's forearm. Longer armrests can be used to support the user's forearm and hand. In some embodiments, the length of the armrest 110 is between about 5 inches and 10 inches, between about 6 inches and about 10 inches, and between about 8 inches and 9 inches. In one embodiment, the armrest has a length of about 8.75 inches. As shown in FIG. 4, the user's leg 278 can be positioned generally underneath the armrest 110 to help keep the user's body properly aligned with the chest support 150. The user's arm 215 can freely move in front of the stool 100 while the chest support 150 comfortably supports the user's chest/stomach 181 to reduce, limit, or substantially eliminate fatigue (e.g., muscle fatigue in the user's arms, shoulders, and/or back), discomfort, and/or pain.

Figure 5:
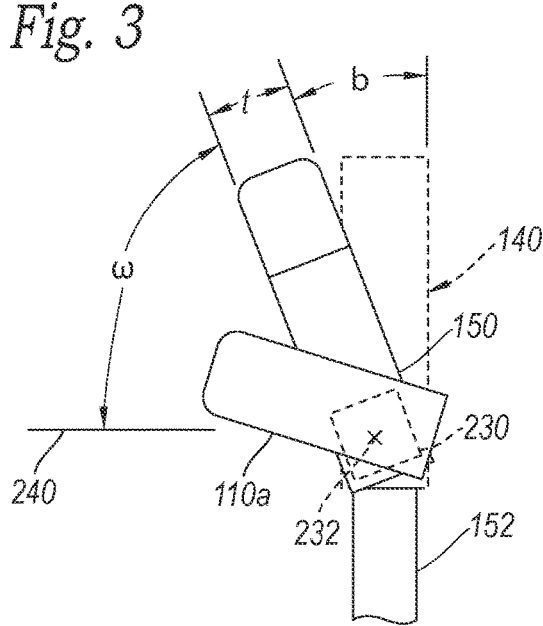
FIG. 5 is a side view of a chest support in different positions in accordance with an embodiment of the present technology.

The chest support 150 can be rotationally fixed to the elongate member 152 and can remain in a substantially vertical orientation during use. In other embodiments, the chest support 150 can be rotated relative to the elongate member 152 for enhanced comfort. FIG. 5 is a side view of the chest support 150 rotated in accordance with an embodiment of the present technology. A pivoting or tilt mechanism 230 (illustrated in phantom line) has an unlocked state and a locked state. In the unlocked state, the pivoting mechanism 230 allows rotation of the chest support 150 about an axis of rotation 232 to move the chest support 150 between a first orientation (e.g., a vertical orientation) to another orientation (e.g., a non-vertical orientation). The axis of rotation 232 can be aligned with the axis of rotation 190 (FIGS. 2 and 3). For example, the axis of rotation 232 can be generally parallel to the axis of rotation 190. However, the axes of rotation 190, 232 can be at other orientations.

The pivoting mechanism 230 can include, without limitation, one or more release mechanisms, hinges, bearings, pins, or combinations thereof and may be capable of manual locking and unlocking. In the locked state, the pivoting mechanism 230 inhibits or prevents rotation of the chest support 150 about the axis of rotation 232. In the unlocked state, the chest support 150 can be rotated about the axis of rotation 232 an angle of rotation β equal to or less than a maximum angle, such as about 70 degrees, 80 degrees, or 90 degrees. In push-button embodiments, the pivoting mechanism 230 can include a button that can be depressed to switch the state of the pivoting mechanism 230. The configuration and operation of the pivoting mechanism 230 can be selected based on the desired reconfigurability of the stool 100. Pivoting mechanisms can also be incorporated into armrests, and in certain embodiments, such pivoting mechanisms can lock armrests at multiple orientations (e.g., a declined orientation, a horizontal orientation, an inclined orientation, a vertical orientation, etc.).

The chest support 150 can be positioned at different angles of inclination ω (i.e., the angle defined by the chest support 150 and a generally horizontal imaginary plane 240). In some embodiments, the angle of inclination ω is equal to or greater than about 30 degrees, 40 degrees, 50 degrees, 60 degrees, 70 degrees, 80 degrees, or 85 degrees. In particular embodiments, the angle of inclination ω is in a range of about 45 degree to about 90 degrees. The chest support 150 can be repositioned at any time during use to minimize, limit, or substantially eliminate fatigue discomfort and/or pain. If the user has to lean over for a significant length of time, the inclination of the chest support 150 can be varied as desired, and the armrest 110a (or armrest 110b) can be locked at a desired position relative to the inclined chest support 150. For example, the angle of inclination ω can be about 45 degrees while one or both armrests 110 are substantially horizontal.

Figure 6:
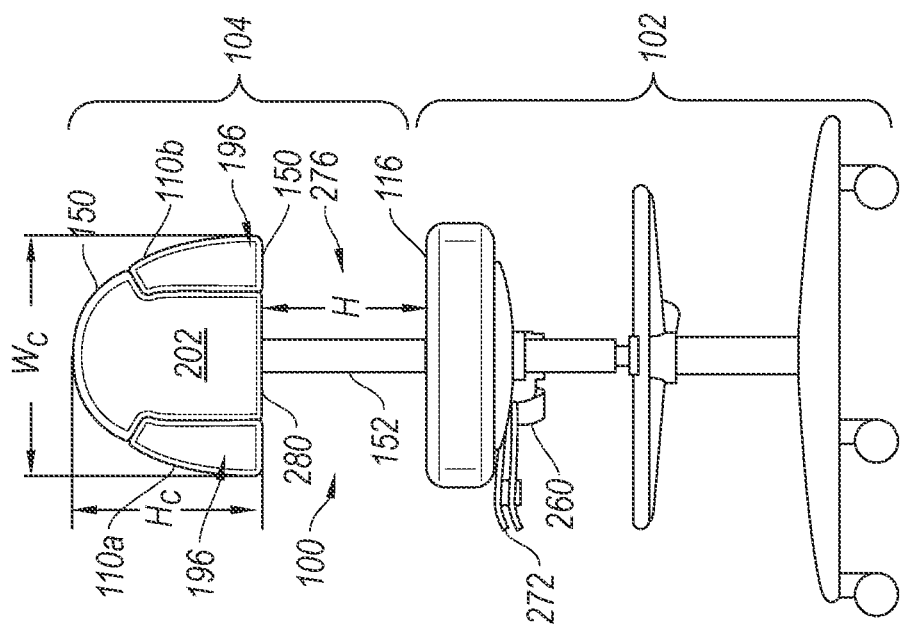
FIGS. 6 and 7 are back views of the stool of FIG. 1.
Figure 7:
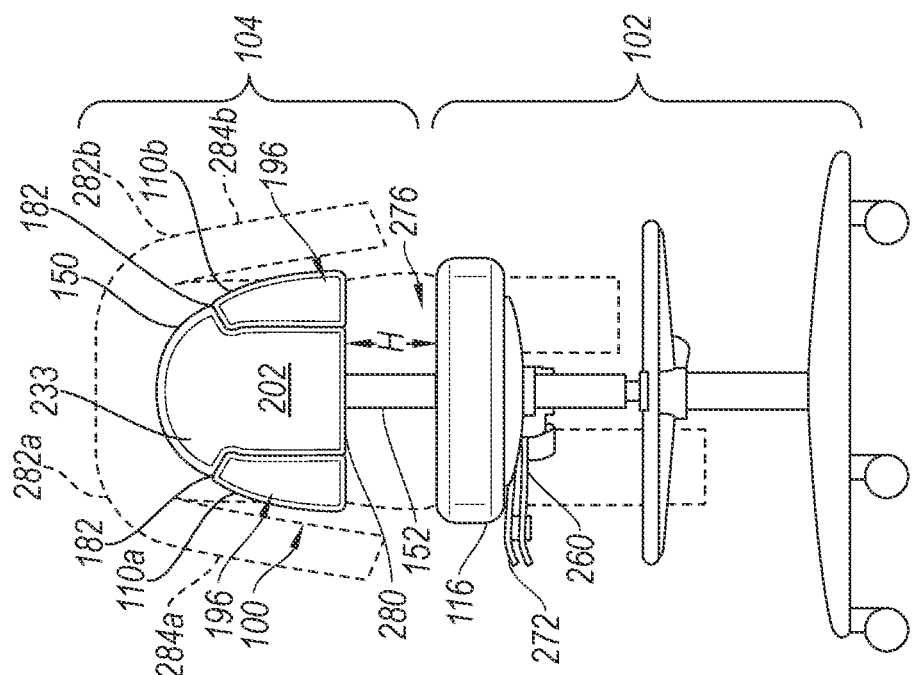

FIG. 6 is a back view of the stool 100 with the chest support 150 at a lowered position. FIG. 7 is a back view of the stool 100 with the chest support 150 at a raised position. The stool 100 can include a vertical adjustment mechanism 260 coupling the elongate member 152 to the seat assembly 102. A user can operate a control element 272 (illustrated as a lever) to switch the adjustment mechanism 260 between a locked state and an unlocked state. In the unlocked state, the adjustment mechanism 260 allows vertical movement of chest support 150 relative to the seat 116 to adjust a height H of a leg-receiving gap 276. In the locked state, the adjustment mechanism 260 can prevent vertical movement of the chest support 150. When the user straddles the elongate member 152, the user's legs can be positioned in the leg-receiving gap 276 and securely held between a bottom 280 of the chest support 150 and the seat 116.

FIG. 6 shows the chest support assembly 104 overlaying a user's torso. Laterally-extending side portions or wings 233 ("side portions 233") of the chest support 150 can extend across most or substantially all the width of the armrest ends 182. In some embodiments, at least about ¼, ½, or ¾ of the width of each armrest 110 is positioned directly underneath respective side portions 233. As shown in FIG. 6, the armrests 110 can be positioned vertically between the side portions 233 and the seat 116. The armrests 110 can be at other positions and have other configurations.

The user's shoulders 282a, 282b can be spaced apart from the chest support 150 and armrests 110 to permit free movement of the user's arms 284a, 284b. In some embodiments, the chest support assembly 104 is generally narrower than the width of the user's torso such that the user can move their elbows along their sides without contacting the chest support assembly 104. In some embodiments, a height $H_c$ (FIG. 7) of the chest support 150 can be in a range of about 5 inches (12.7 cm) to about 1 ft. (30.5 cm), about 6 inches (15 cm) to about 14 inches (36 cm), or other suitable heights selected such that the chest support 150 comfortably supports a user's chest. In one embodiment, the height $H_c$ (FIG. 7) is about 11 inches (28 cm), about 11.5 inches (29 cm), or about 1 ft. (30.5 cm). The width $W_c$ (FIG. 7) of the chest support assembly 104 can be in a range of about 8 inches (20.3 cm) to about 2 ft. (61 cm), about 16 inches (40.6 cm) to about 20 inches (51 cm), about 17 inches (43 cm) to about 19 inches (48 cm). As such, the chest support assembly 104 can be narrower than the user's chest to provide generally unrestricted movement of the user's arms on the front side of the stool 100. In one embodiment, the chest support 150 and armrests 110 are dimensioned to overlay the chest of the user such that most of the surfaces 196, 202 contact the user's chest. The thickness t (FIG. 5) of the chest support 150 and/or armrests 110 can be in a range of about 0.5 inch (1.3 cm) to 2 inches (5 cm). The dimensions of the components of the chest support assembly 104 can be selected based on, for example, the size of the user, desired amount of support, and/or type of activity to be performed. Accordingly, other dimensions can be used, if needed or desired.

Figure 10:
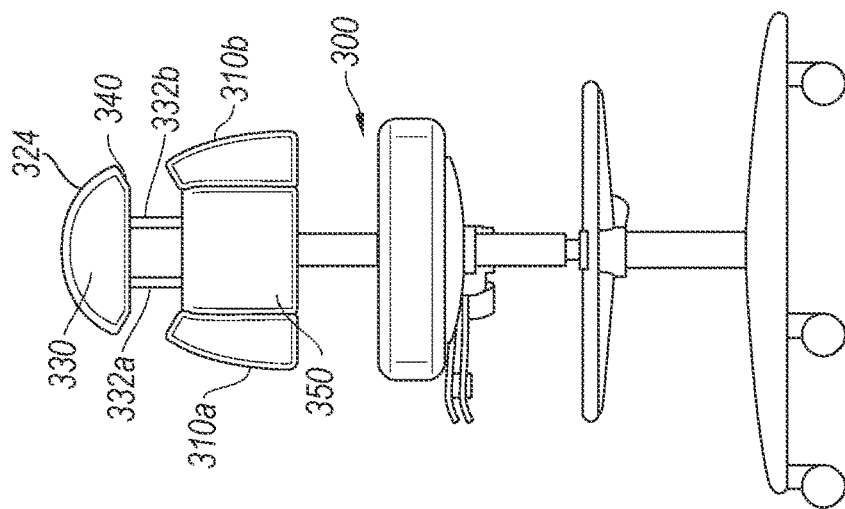
FIG. 10 is a back view of the stool of FIG. 8 with an upper chest support in a raised position.
Figure 9:
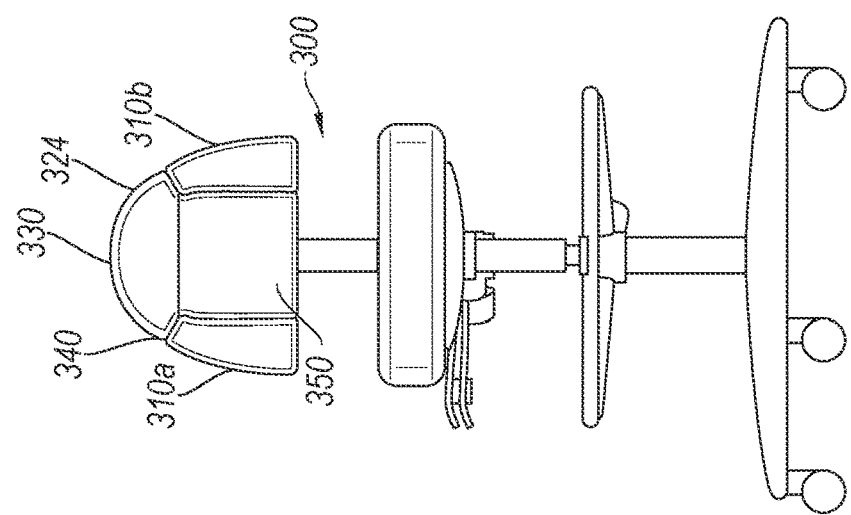
FIG. 9 is a back view of the stool of FIG. 8.
Figure 8:
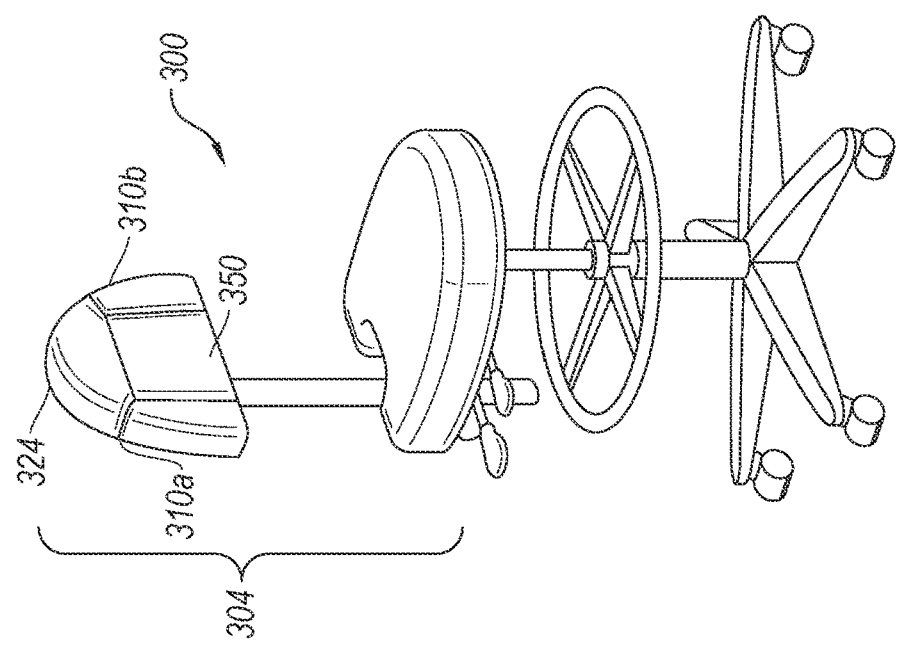
FIG. 8 is an isometric view of a stool with raised armrests in accordance with an embodiment of the present technology.

FIG. 8 is an isometric view of a stool 300 in accordance with an embodiment of the present disclosure. The description of the stool 100 discussed in connection with FIGS. 1 to 7 applies equally to the stool 300, except as detailed below. The stool 300 can include a chest support assembly 304 with armrests 310a, 310b, a chest support 350, and an upper chest support member 324 ("upper support member 324"). The upper support member 324 is moveable between a lowered position (FIGS. 8 and 9) and a raised position (FIG. 10). When the support member 324 is in the lowered position, the chest support assembly 304 is in an unexpanded configuration such that the upper chest support 324 and the chest support 350 define a generally continuous surface for contacting the user's torso. When the support member 324 is in the raised position and spaced apart from the chest support 350, the chest support assembly 304 is in an expanded configuration. The armrests 310 can be raised and lowered independent of the position of the upper support member 324.

Referring now to FIG. 10, the upper support member 324 can include a main body 330 and a pair of rods 332a, 332b (collectively "rods 332"). The main body 330 can be padded and can include a lower portion 340 configured to mate with the armrests 310a, 310b and the chest support 350. The chest support 350 can have a generally square shape (shown in FIGS. 9 and 10) or rectangular shape, but it can have other configurations. When the upper support member 324 is in the lowered position (FIG. 9), the rods 332 can be positioned within the chest support 350. A user can lift upwardly on the main body 330 to raise the support member 324 relative to the chest support 350. The rods 332 can extend from the chest support 350 until the upper support member 324 is at the desired height. In some embodiments, a locking mechanism can be used to lock and unlock the upper support member 324. The amount of travel of the upper support member 324 can be in a range of about 2 inches (5 cm) to about 6 inches (15 cm), about 2 inches (5 cm) to about 5 inches (12.7 cm), or about 2 inches (5 cm) to about 4 inches (10 cm). In certain embodiments, the upper support member 324 can be separated from the chest support 350 by distance equal to or greater than about 1 inch (2.5 cm), 2 inches (5 cm), 3 inches (7.6 cm), 4 inches (10 cm), or 5 inches (12.7 cm) when in the fully deployed position.

FIG. 11 is an isometric view of a portion of a stool 400 in accordance with an embodiment of the present technology. The stool 400 can include a chest support assembly 410 and a seat assembly 412. The chest support assembly 410 can include a chest support 420 and a frame 422, which couples the chest support 420 to a seat 430. The chest support 420 can have an upside down V-shape or U-shape. The frame 422 can be fixedly coupled to the chest support 420 by, for example, one or more brackets, fasteners (e.g., screws, nut and bolt assemblies, etc.), or the like. The frame 422 can include rods 440a, 440b (collectively "rods 440") slidably received by receivers 450a, 450b, respectively, of the seat assembly 412. One or more pins can be removed from holes 460 to vertically move the frame 422, and the pins can be inserted in the holes 460 to lock the chest support assembly 410 to the seat assembly 412.

FIG. 12 is a side view of the chest support assembly 410 of FIG. 11. A hinge (not shown in FIG. 12) can rotatably couple the chest support 420 to the frame 422. A tilt mechanism 461 can be unlocked by removing a pin, and the chest support 420 can be rotated about an axis of rotation 462. The pin can be inserted into one of the holes 464 to lock the chest support 420 at the desired angle of inclination. Other types of mechanisms (e.g., tilt mechanisms, pivot mechanisms, etc.) can be utilized.

FIG. 13 is a side view of a tilt mechanism 484 for tilting the chest support assembly 410. A pin can be removed from one of the holes 480 to rotate the frame 422, as indicated by arrow 490. When the chest support 420 (shown at two different positions) is at the desired orientation, the pin can be inserted through the appropriate hole 480 to lock the chest support assembly 410.

To perform a task at relative low locations (e.g., to tattoo a lower body part, such as a client's leg when the client is sitting in a chair), the chest support 420 can be tilted forward. Once the chest support 420 is at the desired orientation, the tilt mechanism 481 can be locked. The user can straddle the chest support assembly 410 and can comfortably lean on the chest support 420 for a relatively long period time to perform the task. Although not shown in FIGS. 11-13, armrests can be incorporated into the chest support assembly 410. For example, armrests can be rotatably coupled to the sides of the chest support 420.

Figure 14:
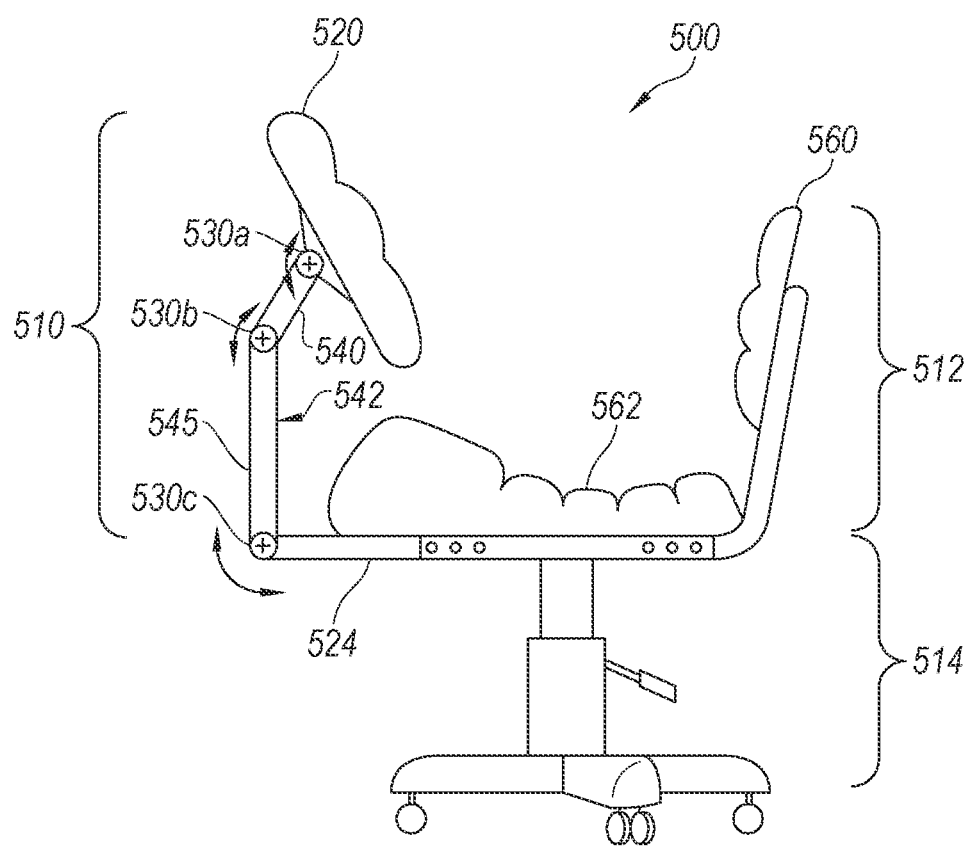
FIG. 14 is a side view of a chair in accordance with an embodiment of the present technology.

FIG. 14 is a side view of a chair 500 in accordance with an embodiment of the present technology. The chair 500 can include a chest support assembly 510, a back support assembly 512, and a seat assembly 514. The chest support assembly 510 can include a chest support 520 and a connector apparatus 542. In some embodiments, including the illustrated embodiment, the connector apparatus 542 includes members 540, 545 and pivots 530a, 530b, 530c. The elongated member 540 can extend between the pivots 530a, 530b. The elongated member 545 can extend between the pivots 530b, 530c. The back support assembly 512 can include a back support 560 for supporting the user's back. The user can sit on a seat 562 and either lean rearward against the back 560 or lean forward against the chest support 520.

Figure 15:
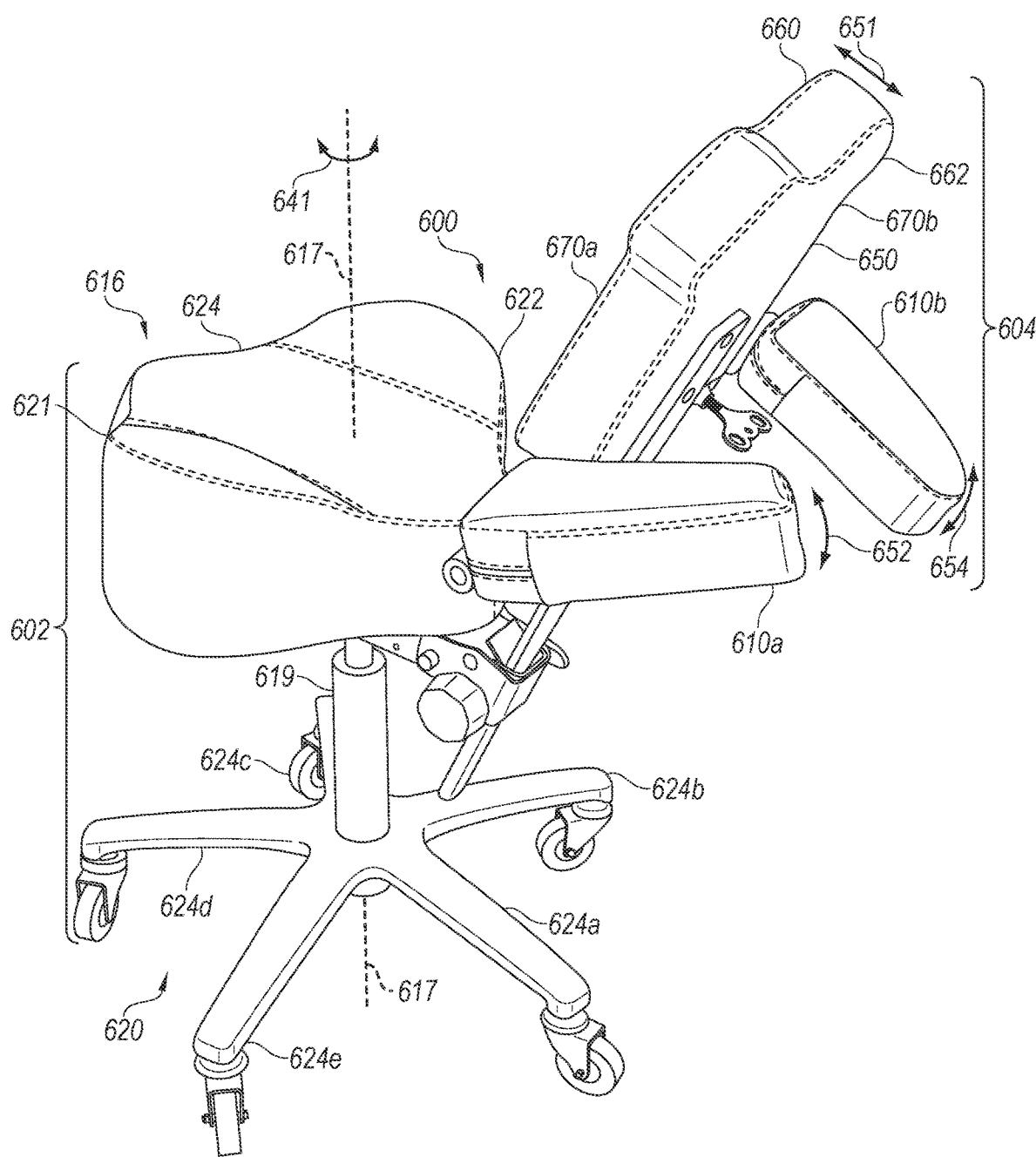
FIG. 15 is an isometric view of a stool with a tilted chest support, an inclined right armrest, and a declined left armrest in accordance with an embodiment of the present technology.

FIG. 15 is an isometric view of a stool 600 in accordance with an embodiment of the present technology. The stool 600 can include a seat assembly 602 and a chest support assembly 604. When a user sits on the seat assembly 602, the user's chest can rest comfortably against the chest support assembly 604 such that the user's arms are free to move in front of the stool 600. Armrests 610a, 610b can be moved between preset positions to ergonomically support the user's arms and, in some embodiments, can be removed from a chest support 650. The chest support 650 can be rotated (indicated by arrow 651) and the armrests 610a, 610b (collectively "armrests 610") can be rotated (indicated by arrows 653, 654) to provide a large number of ergonomic configurations. The illustrated chest support 650 and right armrest 610a are at inclined orientations, and the left armrest 610b is at a declined orientation.

The seat assembly 602 can include a contoured seat 616 and a base assembly 620 carrying the seat 616. The seat 616 has flared or sloped regions 621, 622 and a central region 624. The regions 621, 622 can be sufficiently sloped or angled to help keep the user generally centered on the central region 624. The base assembly 620 can include a base member 619 and wheels 624a, 624b, 624c, 624d, 624e (collectively "wheels 624"). The base member 619 can include a hydraulic assembly that can raise and lower the seat 616, which can rotate (indicated by arrow 641) about a vertical axis of rotation 617. The chest support 650 has a backside 660 for supporting an occupant, a front side 662 facing away from the occupant, and armrest-receiving portions 670a, 670b having complementary shapes with the armrests 610a, 610b, respectively.

Figure 16:
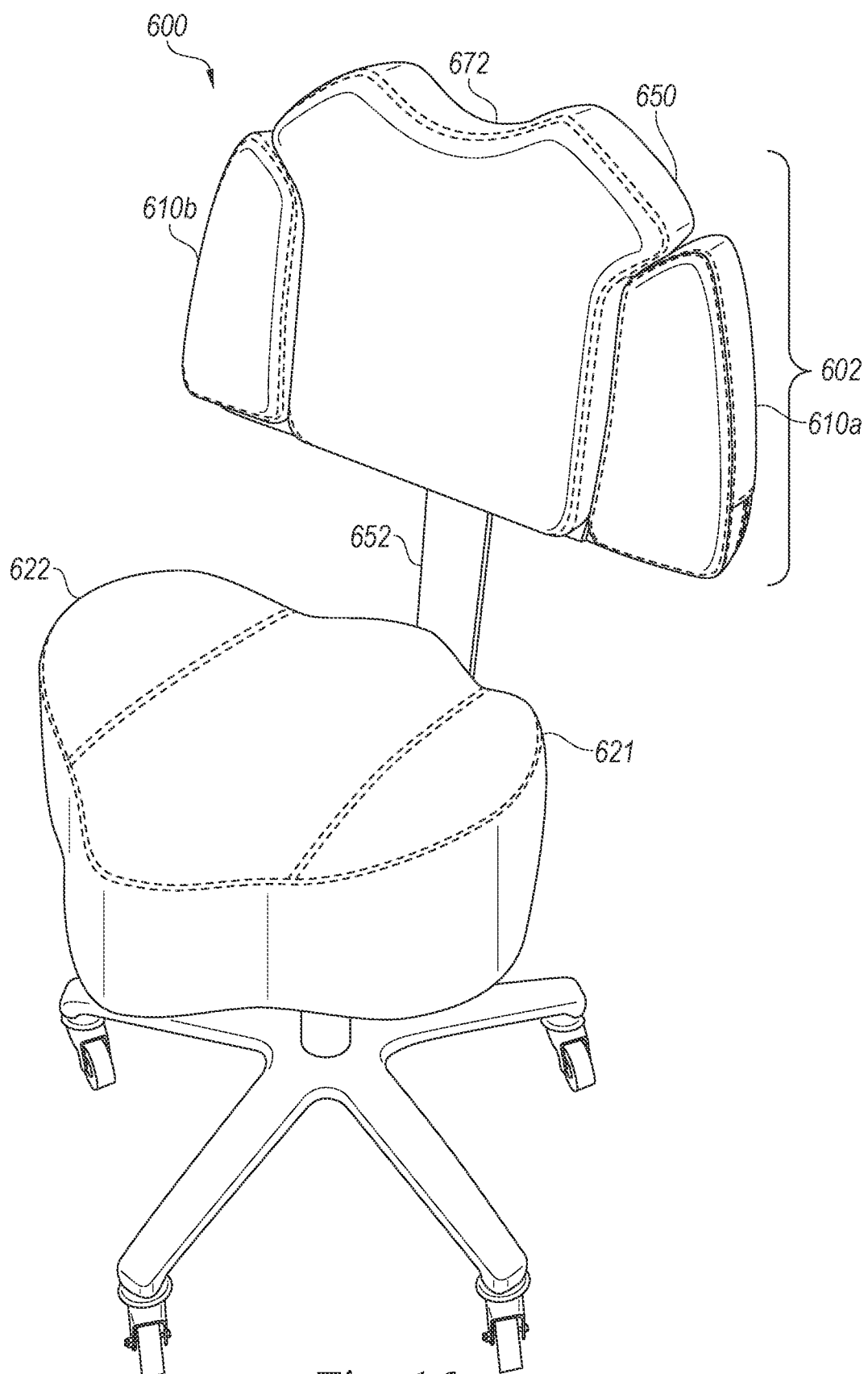
FIG. 16 is an isometric view of the stool with stowed armrests.
Figure 17:
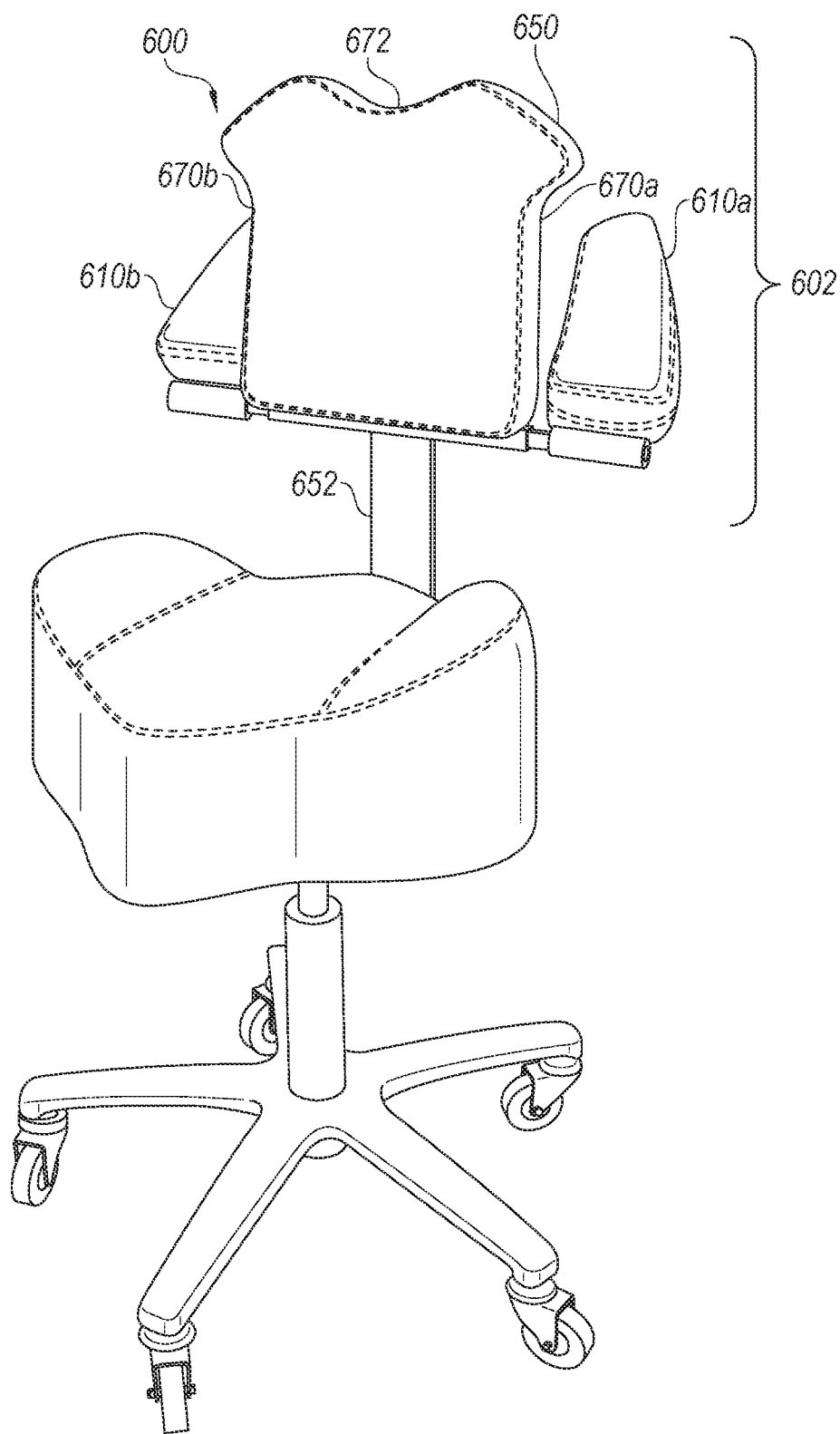
FIG. 17 is an isometric view of the stool with partially lowered armrests.

FIG. 16 is an isometric view of the stool 600 with stowed armrests 610, and FIG. 17 is an isometric view of the stool 600 with lowered armrests 610. Referring now to FIG. 16, the stowed armrests 610a, 610b are located in the armrest-receiving portions 670a, 670b, respectively, such that when a user straddles an elongate member 652 of the chest support assembly 604, the sloped seat regions 621, 622 can inhibit lateral movement of the user to help keep the user's torso centered relative to the chest support 650. The chest support 650 can have a contoured upper portion 672 that is complementary (e.g., shaped to receive) with a portion of the user's body. In some embodiments, the upper portion 672 can be a concaved or recessed region with a U-shaped profile, a V-shaped profile, or other shaped profile for matching the user's body, such as the user's neck and/or chin.

Figure 18:
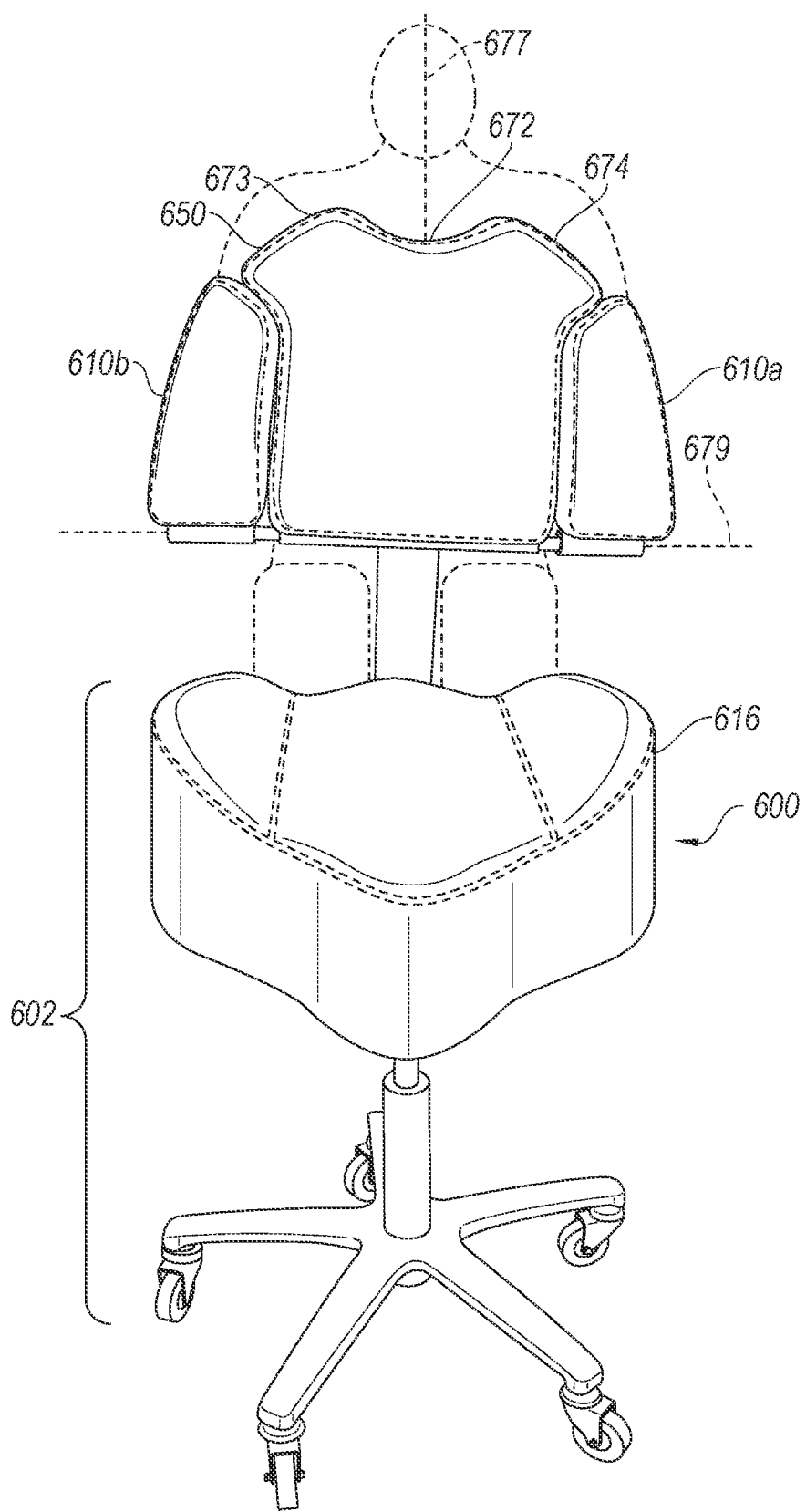
FIG. 18 is a back view of the stool with stowed armrests and a user sitting on the stool.

FIG. 18 shows a user (illustrated in dashed line) sitting on the seat 616. The user's chin is positioned generally above the contoured upper portion 672 positioned centrally along the chest support 650 to provide a relatively large amount of unrestricted movement of the user's head. The shoulder regions or wings 673, 674 can extend laterally outward from the upper portion 672 and can support the user's shoulders when the user leans forward. The armrests 610a, 610b can be moved away from a center plane 677 of the stool 600 to unlock the armrests such that the armrests are freely rotatable about an axis of rotation 679. Locking/unlocking the armrests 610 is discussed in connection with FIGS. 24 and 25.

Figure 19:
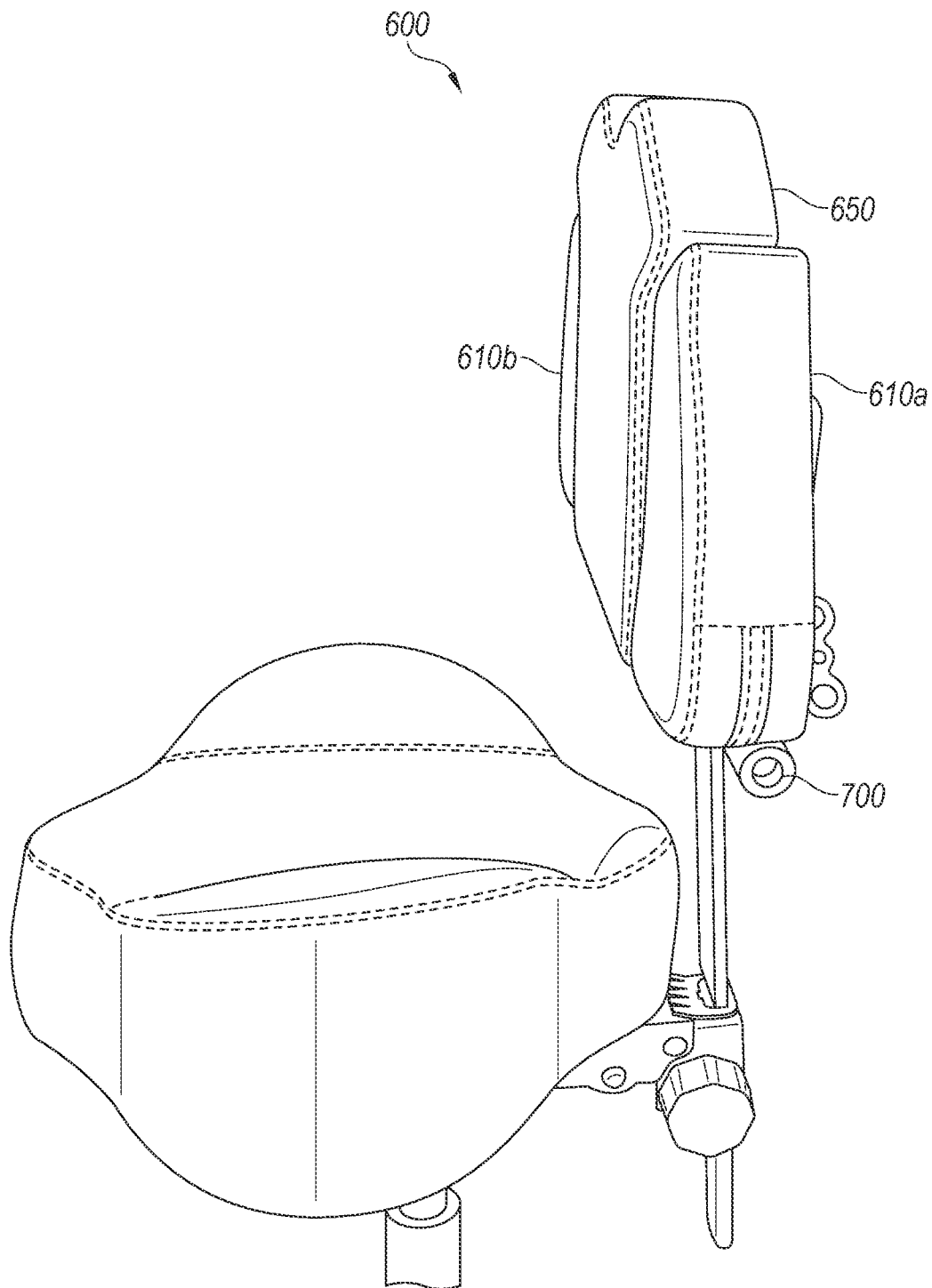
FIGS. 19-23 are side views of the stool with armrests in different positions.
Figure 20:
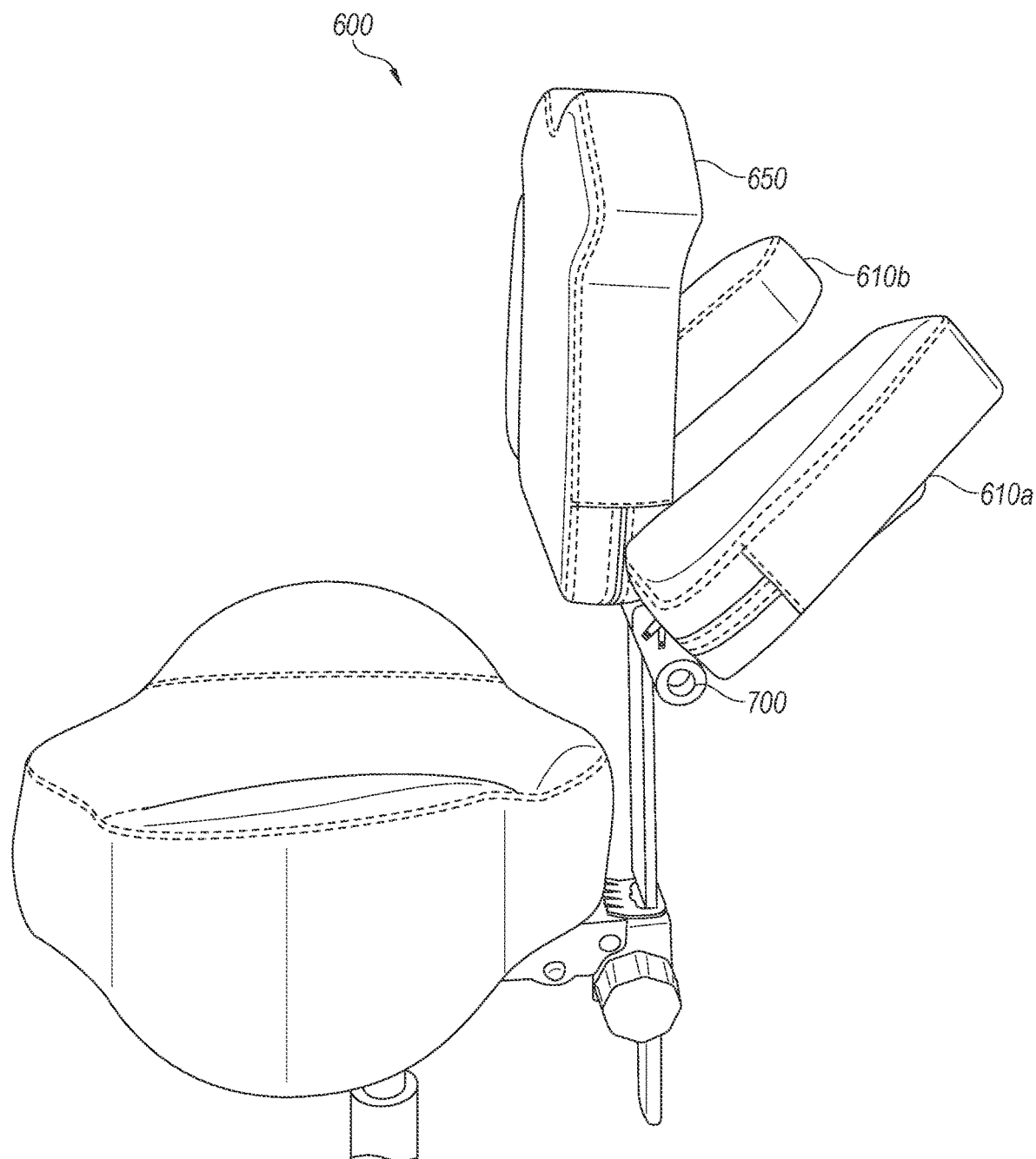
Figure 21:
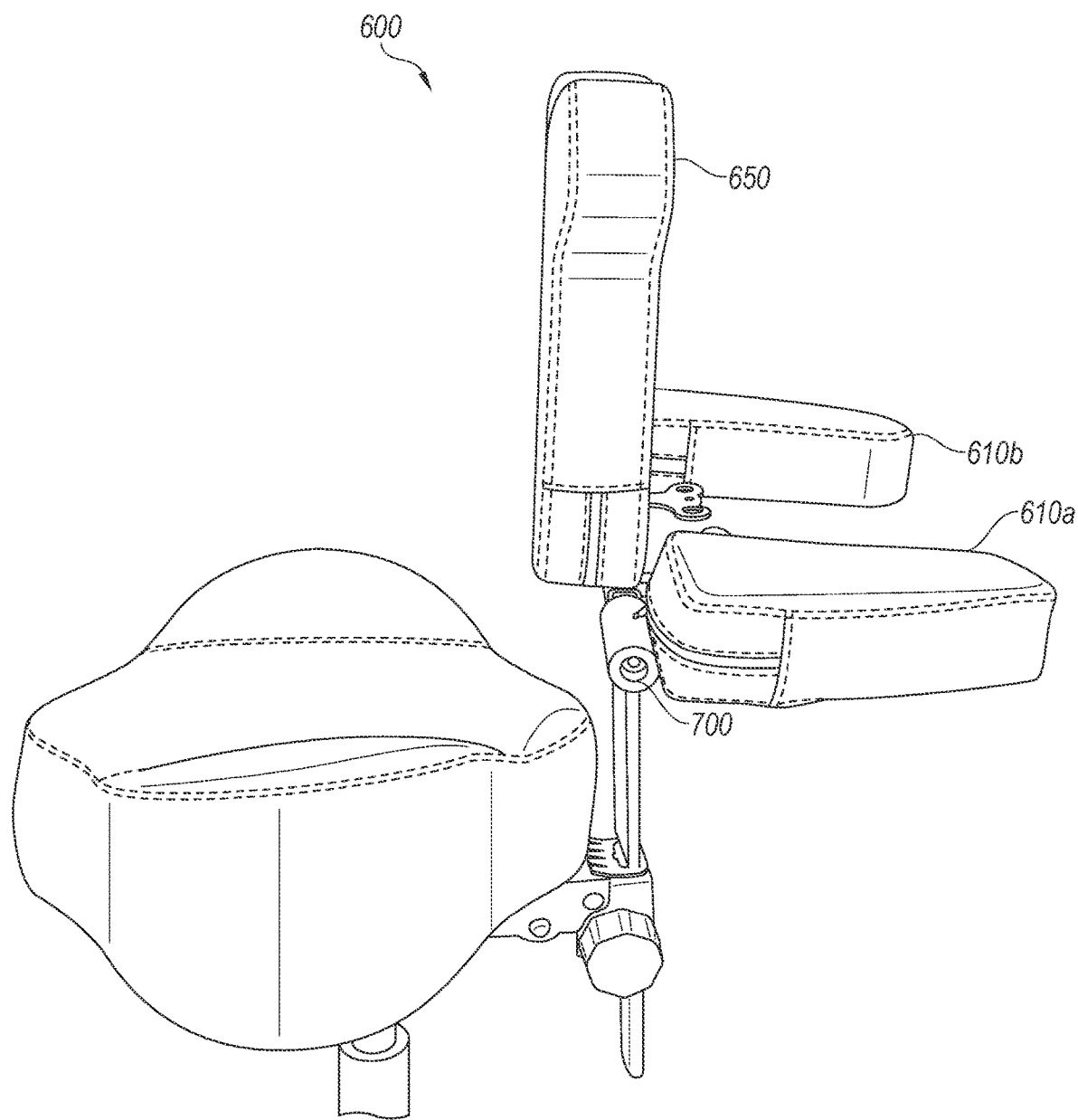
Figure 22:
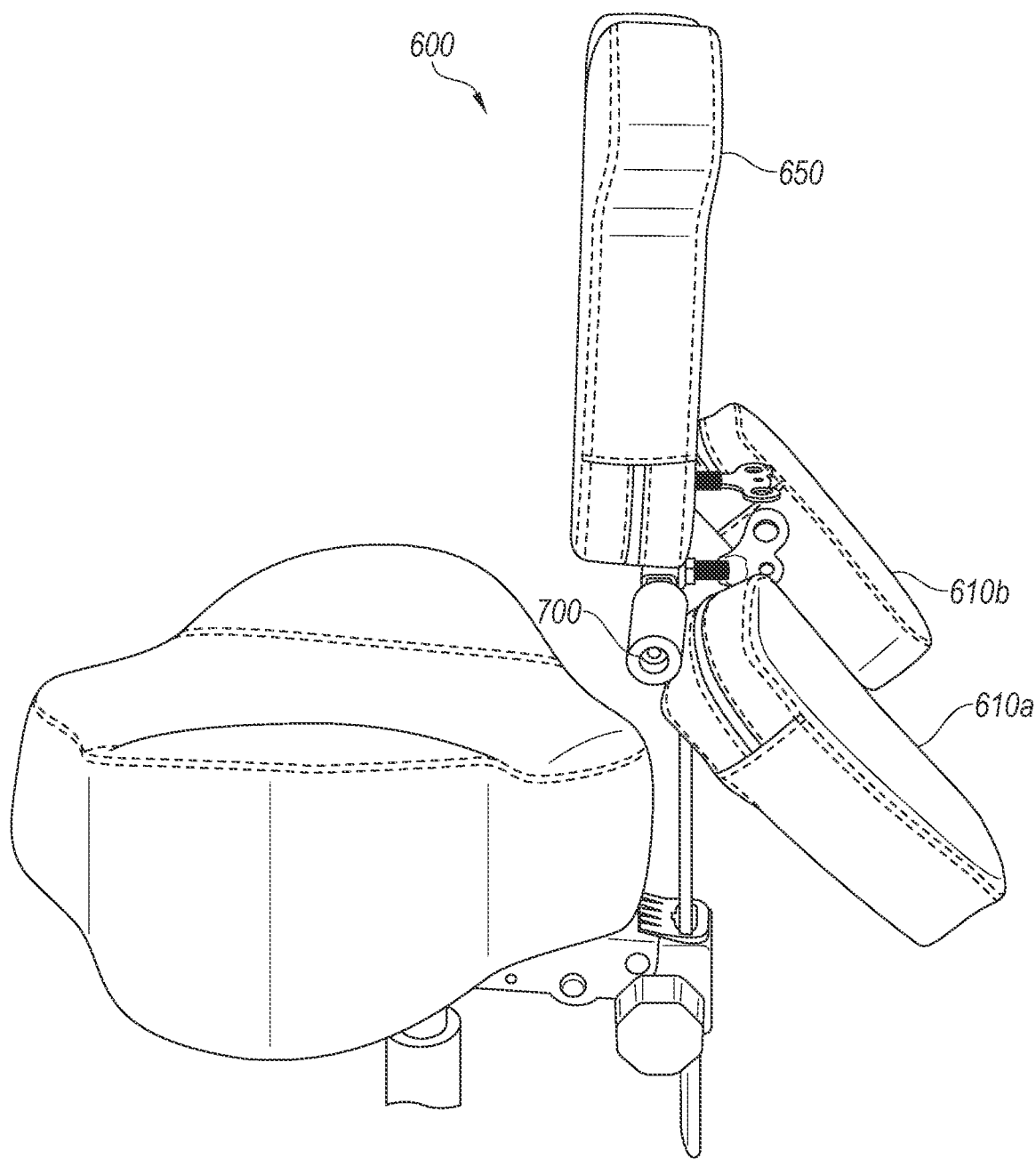
Figure 23:
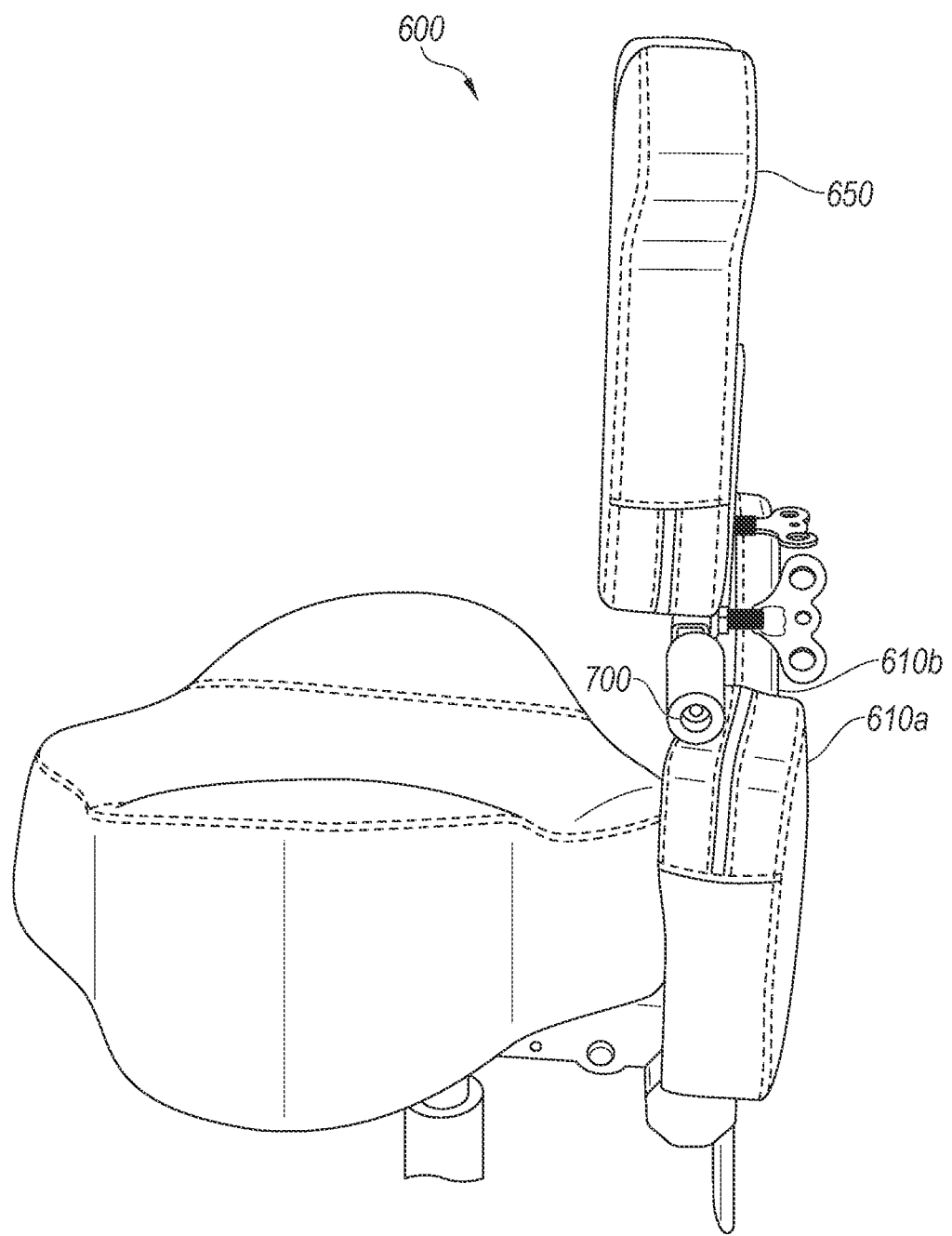

FIGS. 19-23 show the armrests 610 at different angular positions. In particular, FIG. 19 shows the armrests 610 at stowed positions. FIG. 20 shows the armrests 610 at inclined orientations. FIG. 21 shows the armrests 610 at generally horizontal orientations. FIG. 22 shows the armrests 610 at declined orientations. FIG. 23 shows the armrests 610 in fully lowered positions in which the armrests 610 extend in a direction that is generally parallel to a plane of the chest support 650. The lowered armrests 610 of FIG. 23 can help support a user's lower back or buttock when the user's back is against the chest support 650 serving as a back support. The number of angular positions of the armrests 610a, 610b can be selected based on the use of the stool 600 and can be, for example, 2 to 25 preset positions, 5 to 20 preset positions, etc. In some embodiments, an armrest positioner assembly 700 (FIG. 23) can allow the armrests 610 to be moved between about 15 preset angular positions and can include one or more pivoting mechanisms, release mechanisms, hinges, bearings, pins, or combinations thereof. One embodiment of the armrest positioner assembly 700 is discussed in connection with FIGS. 24 and 25.

Figure 24:
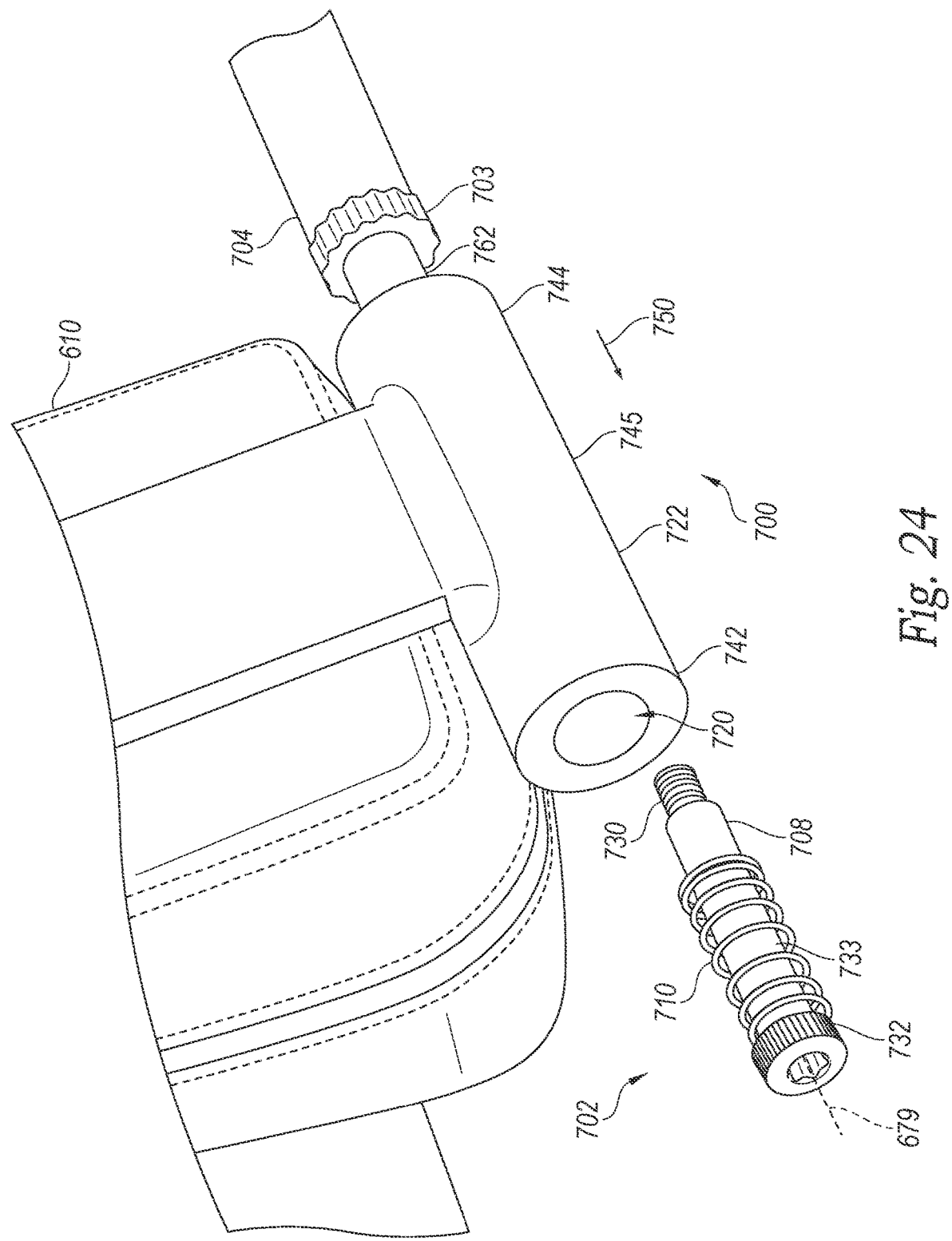
FIG. 24 is an exploded isometric view of components of an armrest positioner assembly in accordance with an embodiment of the present technology.

FIG. 24 is an exploded isometric view of the armrest positioner assembly 700 including a biasing assembly 702 and a rod 704. The biasing assembly 702 can bias the armrest 610 toward a locked state and can include a fastener 708 and a biasing member 710 surrounding the fastener 708. The fastener 708 has an externally threaded end 730 for coupling to the rod 704, a head 732 for contacting the biasing member 710, and a main body 733. The fastener 708 can be located in a passageway 720 of a receiver 722 such that the biasing member 710 is compressed between a stop or a shoulder inside the receiver 722 and the fastener head 732. The biasing member 710 can include one or more springs (e.g., helical springs, compression springs, etc.) that can urge the receiver 722 towards engagement features 703 of the rod 704.

Figure 25:
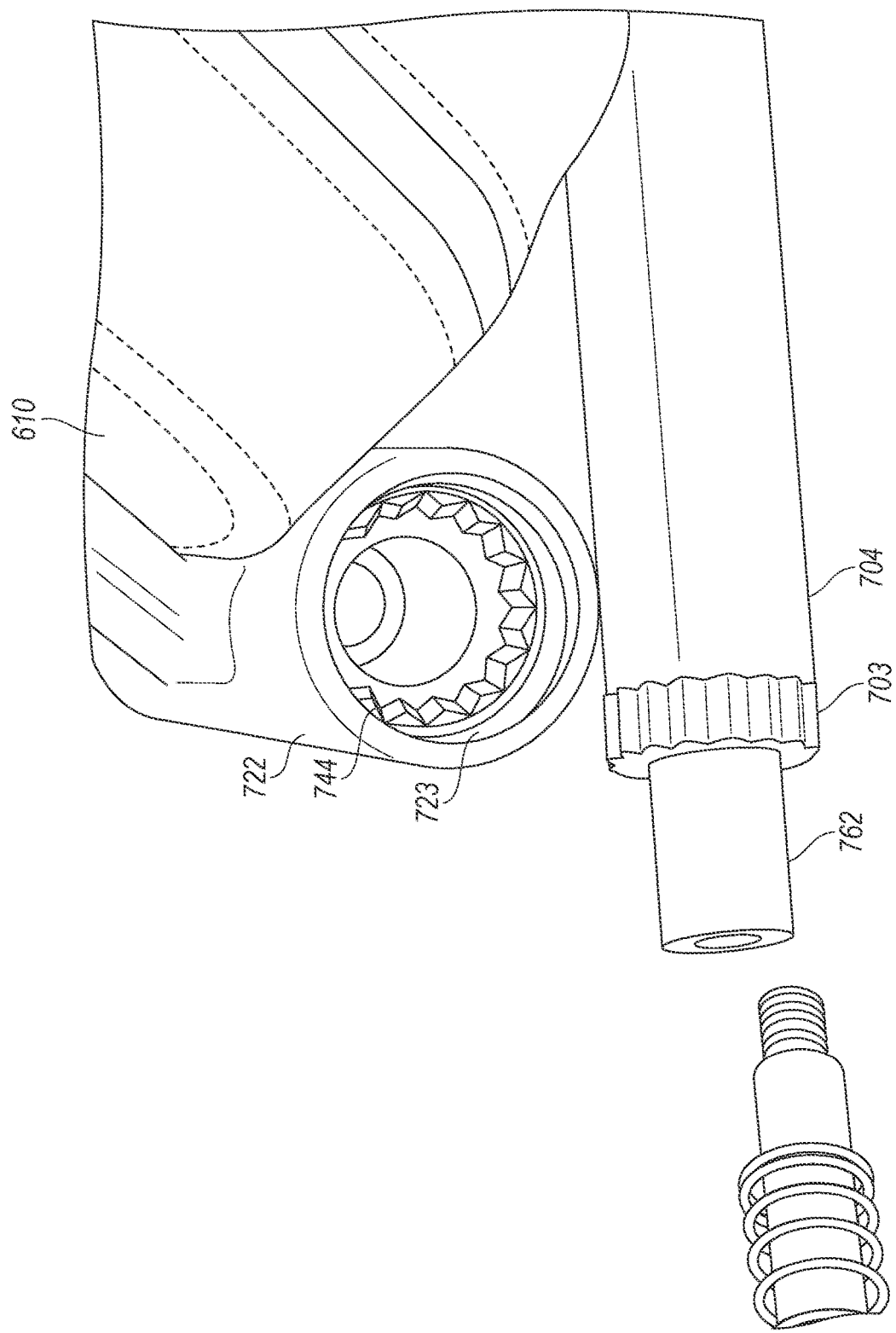
FIG. 25 shows components of the armrest positioner assembly.

The receiver 722 can be a hollow member (e.g., a tubular member) or holder fixed to the armrest 610 and can have ends 742, 744 and a main body 745. The end 742 is configured to receive the head 732 of the fastener 708, and the end 744 is configured to receive a pin 762 threadably coupleable to the threaded end 730. FIG. 25 shows the receiver end 744 with engagement features in the form of teeth 723 for engaging teeth 703 of the rod 704. In a locked state, the teeth 723 can mesh with the teeth 703 to rotationally fix the armrest 610 relative to the chest support. When a user manually moves the receiver 722 away from the teeth 703 (indicated by arrow 750 in FIG. 24) by overcoming the biasing of the biasing member 710, the teeth 723 (FIG. 25) can disengage and move away from the teeth 703. The armrest 610 can then freely rotate about the axis of rotation 679 (FIGS. 18 and 24) defined by the fastener 708 and pin 762. Once the armrest 610 is at a desired position, the user can allow the biasing member 710 to urge the armrest 610 back to the rotationally locked state in which the teeth 723 engage the teeth 703. The number and size of the teeth can be selected based on the desired number of preset angular positions (e.g., 2-20 positions, 5-17 positions, 6-15 positions, 15 positions, etc.) of the armrest 610.

Figure 26:
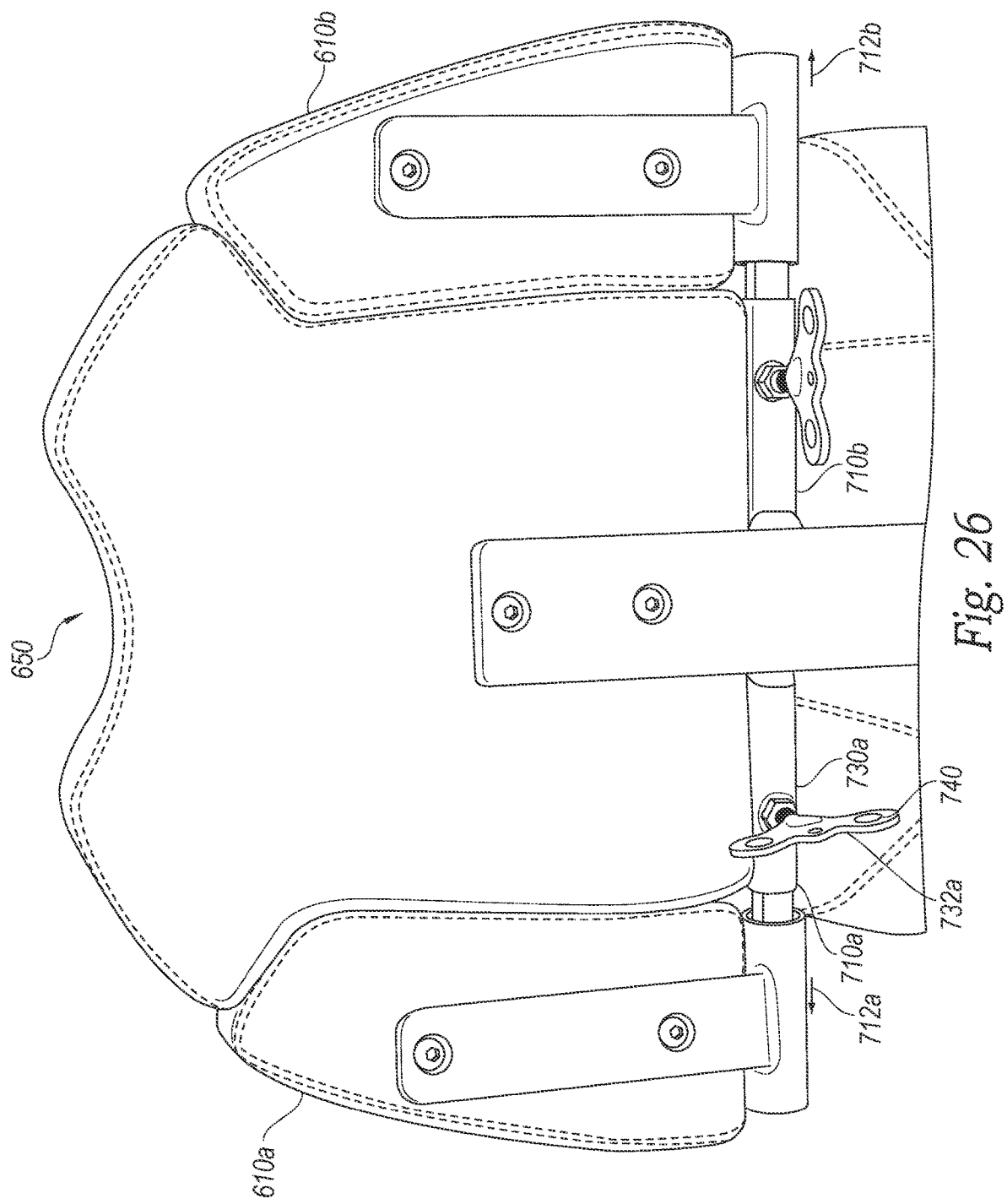
FIG. 26 is a front view of a chest support with stowed armrests in laterally undeployed positions.
Figure 27:
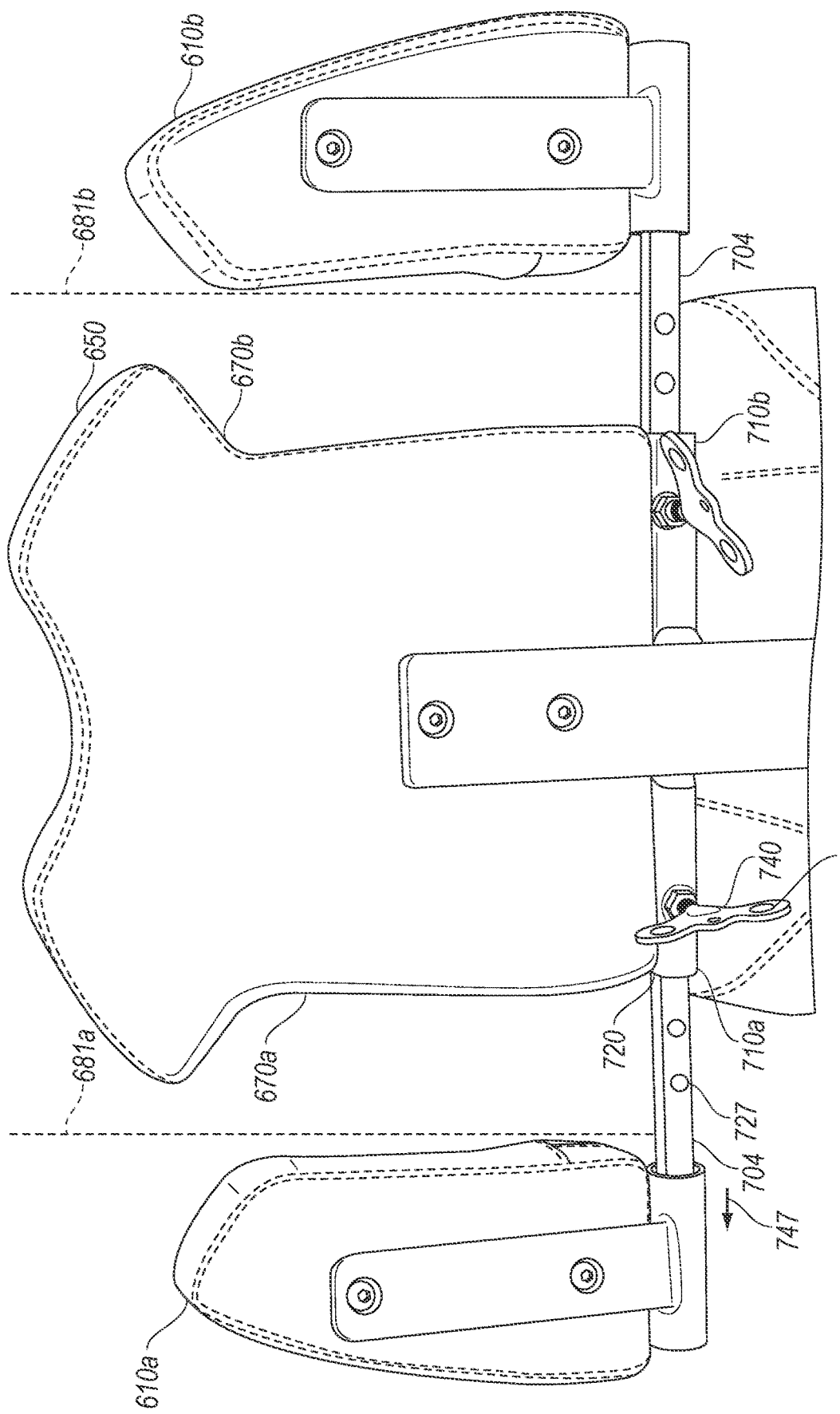
FIG. 27 is a front view of the chest support with armrests in laterally deployed positions.

FIGS. 26 and 27 are front views of the chest support 650 with extension mechanisms 710a, 710b having locked configurations for laterally locking the respective armrests 610a, 610b and deployed configurations for allowing lateral movement of the respective armrests 610a, 610b. FIG. 26 shows the armrests 610 at laterally undeployed positions. The armrests 210 can be moved laterally outward (indicated by arrows 712a, 712b in FIG. 26) to laterally deployed positions shown in FIG. 27.

Referring now to FIG. 27, the extension mechanisms 710a, 710b can be generally similar to each other, and accordingly, the description of one extension mechanism 710a, 710b applies equally to the other extension mechanism 710a, 710b unless indicated otherwise. The extension mechanism 710a can include the rod 704, a receiver 735 (e.g., a hollow tube) that receives the rod 704, and a locking device 732. The rod 704 can include an array of receiving-features 727 (e.g., holes) for receiving the locking device 732, which can include one or more pins, handles, or other features for locking/unlocking the rod 704. In one embodiment, the locking device 732 includes a handle 740 that can be rotated move a pin of the locking device 732 into and out of the holes 727. When the locking device 732 is in an unlocked state, the rod 704 can be extended from the receiver 735 (indicated by arrow 747). The locking device 732 can be rotated to move a pin into one of the holes 727 when the armrest 610a is positioned at the desired lateral position. The extension mechanisms 710a, 710b can be used to increase or decrease the spacing between the armrests 610a, 610b based on, for example, the width of the user's shoulders, the desired spacing between the user's forearms, or other criteria. In some embodiments, the armrests 610a, 610b can be moved away from the chest support 650 at least about 1 inch (2.5 cm), 2 inches (5 cm), 3 inches (7.6 cm), 4 inches (10 cm), or 5 inches (12.7 cm). In one embodiment, each armrest 610a, 610b can be moved about 2.5 inches (6.4 cm) away from the chest support 650 to be moved to the fully deployed position.

As shown in FIG. 27, when the armrests 610a, 610b are in the fully laterally deployed positions, the armrest 610a and the chest support 650 can be positioned on opposite sides of an imaginary vertical plane 681a. The armrest 610b and the chest support 650 can be positioned on opposite sides of an imaginary vertical plane 681b. Accordingly, the armrests 610a, 610b can be positioned completely outside of the armrest-receiving portions 670a, 670b.

Figure 28:
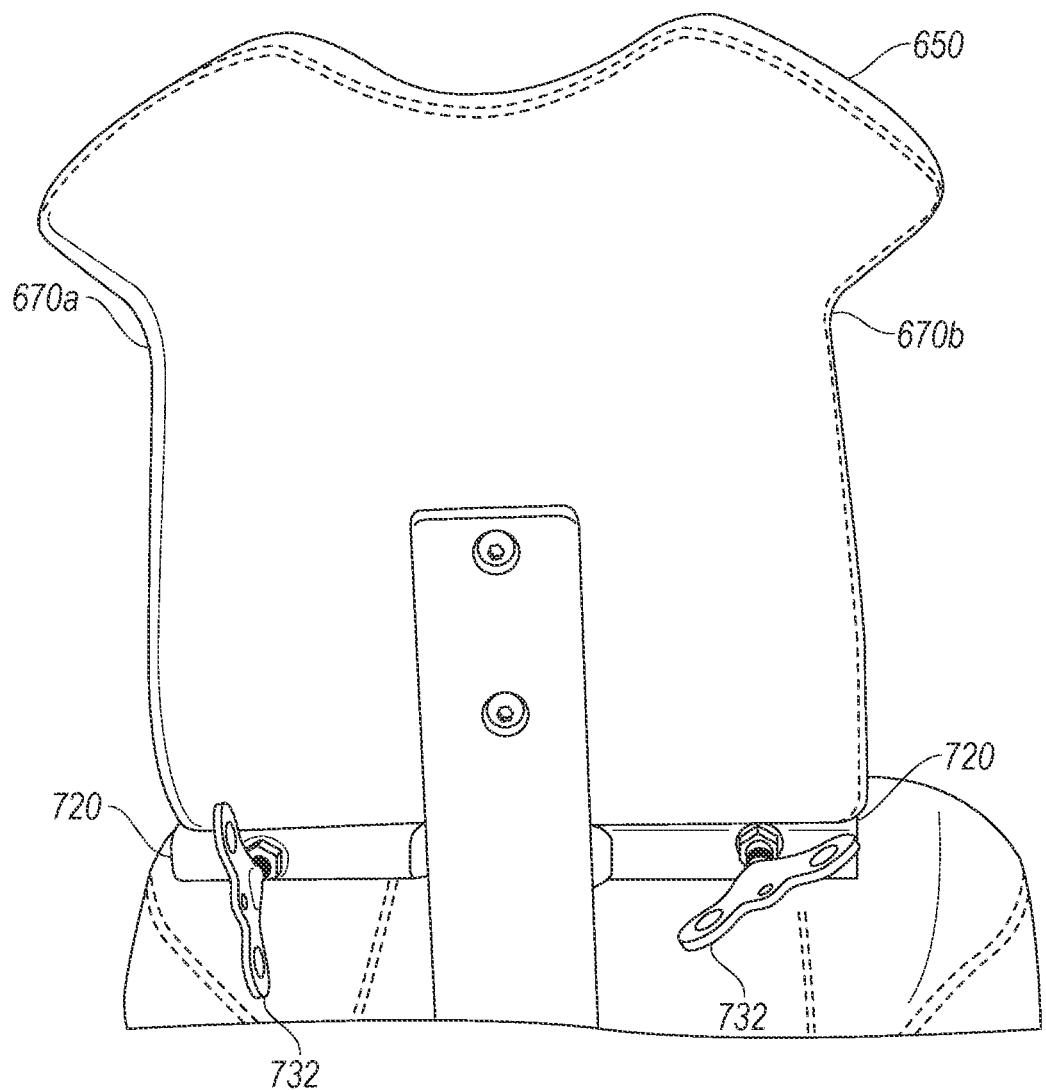
FIG. 28 is a front view of the chest support with armrests removed.

Additionally, when the locking devices 732 are unlocked, the armrests 610 can be removed from the chest support 650. FIG. 28 is a front view of the chest support 650 after the armrests 610a, 610b have been removed. When a user faces the chest support 650, the user's chest and shoulders can rest comfortably against the chest support 650 while the user's arms are unencumbered to provide a relatively large amount of arm movement. For example, the armrest-receiving portions 670a, 670b provide openings through which the user's arms can freely pass. The armrests 610 can be reinstalled by inserting the rods in the respective receivers 735 and sliding the rods to the desired position. Once the armrests 610 are at the desired location, the locking devices 732 can lock the armrests 610 to inhibit lateral movement of the armrests 610 relative to the chest support 650.

Figure 29:
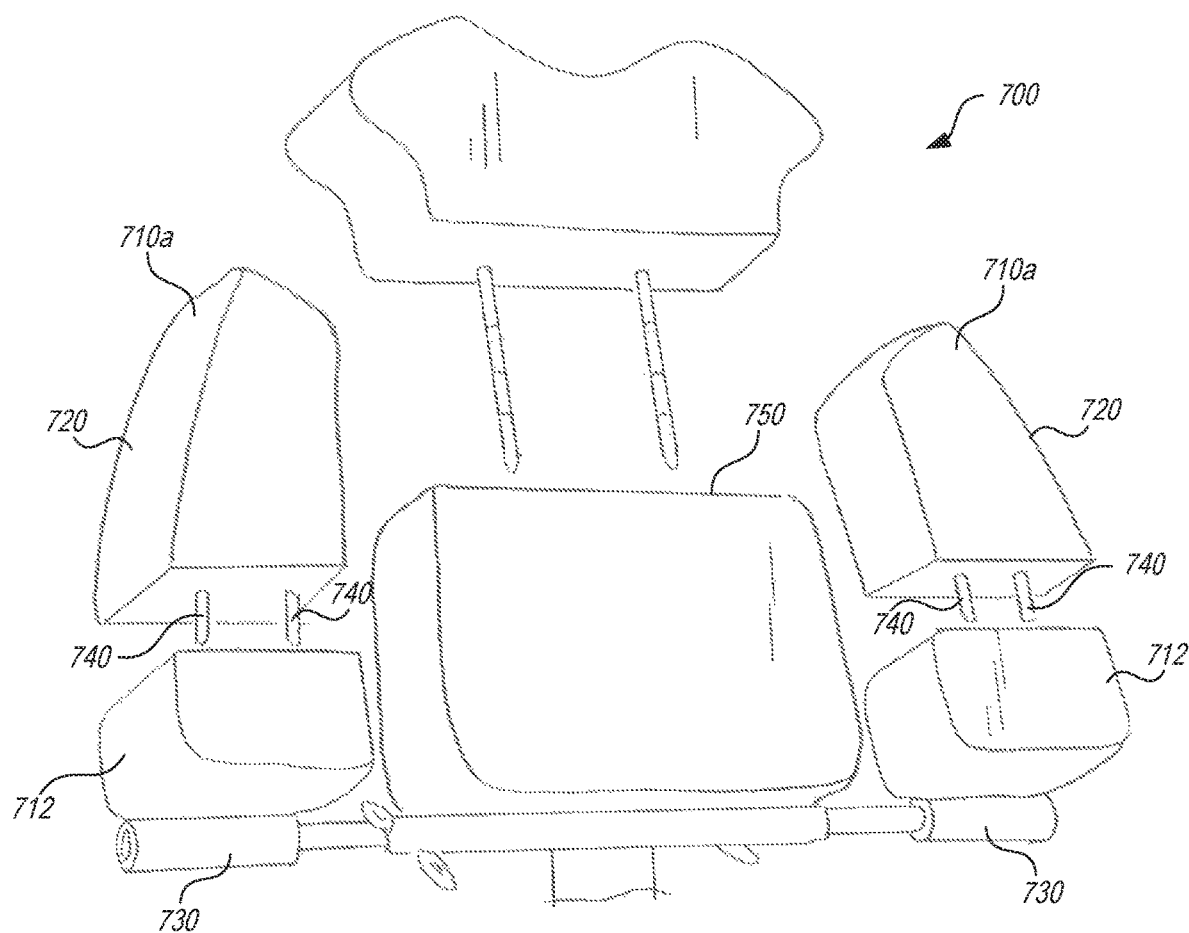
FIG. 29 is an isometric view of a portion of a stool with multi-piece armrests.

FIG. 29 is an isometric view of a portion of a stool 700 with extendable armrests. The stool 700 can be generally similar to the stool 600 of FIG. 22 except as detailed below. The stool 700 includes multi-piece armrests 710a, 710b (collectively "armrests 710") on opposite sides of a chest support 750. Each armrest 710 can include a base 712 and a movable elongate body 720. The base 712 can be connected to the chest support 750 by armrest positioner assemblies or connectors 730. The elongate bodies 720 can each include one or more rods or connectors 740 that can be inserted into corresponding openings (not shown) in the base 712. In some embodiments, the rods 740 can have notches or other features for locking the elongate body 720 at different positions relative to the bases 712. The illustrated armrests 710 have been moved from an unextended configuration in which the elongate bodies 720 are adjacent to or contact the bases 712 to the illustrated extended configuration in which the elongate bodies 720 are spaced apart from the bases 712. To remove one of the elongate bodies 720, that elongate body 720 can be moved away from the base 712. Other stools disclosed herein can also have multi-piece armrests with portions that can be moved away from or towards one another.

The stools 100, 300, or 400 discussed above can also include extension mechanisms for adjusting the lateral position of armrests. For example, the stool 100 of FIG. 1 can include extension mechanisms that allow simultaneous or sequential horizontal movement of the armrests 110a, 110b to provide additional ergonomic positions of the user. The stools and chairs discussed herein can be used in a wide range of settings, including tattoo parlors, medical settings, massage parlors, salons, spas, or other desired settings. In tattoo parlors, a person receiving a tattoo can sit on the stools discussed in connection with FIGS. 1-13 and 15-28 or the chair discussed in connection with FIG. 14. In a single tattoo session, stools 100, 300, 400, 600 or chair 500 can be alternatively used by the client. The client and tattoo artists can simultaneously sit on stools or chairs disclosed herein. In medical settings, patients and/or medical practitioners (e.g., physicians, nurses, etc.) can sit on stools disclosed herein. In some procedures in which a physician inspects or operates on a patient's arm, the patient can sit in one of the stools disclosed herein and the armrest can help support the patient's arm at a desired position. The physician can apply a relatively large amount of pressure to the patient's arm without causing significant movement of the patient's arm. Additionally, straps, restraints, or other features can be incorporated into the armrests (or other components of the stools or chairs) to inhibit or limit movement of the user's arms or other body parts. The stools and chairs disclosed herein can also be used to support a user's arms when typing or performing other repetitive tasks that can often cause discomfort or pain.

Accordingly, the embodiments, features, and methods and techniques described herein may be incorporated into other types of support apparatuses (e.g., stools and chairs) used in a wide range of settings. In some embodiments, the apparatuses disclosed herein include one or more of the features, systems, devices, materials, methods and techniques described in U.S. patent application Ser. No. 12/876,953 (now U.S. Pat. No. 8,651,569), which is incorporated herein by reference in its entirety. For example, the stools and chairs discussed herein can include hydraulics systems, hinges, locking mechanisms, or other components disclosed in U.S. patent application Ser. No. 12/876,953. In some procedures, a person receiving a tattoo can be supported by one of the apparatuses disclosed in U.S. patent application Ser. No. 12/876,953 while the tattoo artist sits on the stools disclosed herein. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patent application Ser. No. 12/876,953. All applications and patents discussed herein are incorporated by reference herein in their entireties.

Unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A stool, comprising:
a seat assembly; and
a chest support assembly coupled to the seat assembly and including:
a chest support including an upper support member and a lower support member, wherein the upper support member has a padded main body movable away from the lower support member, and
an armrest movable between a stowed locked position and a deployed position, wherein the armrest, in the stowed locked position, and the chest support together define a chest support surface and the armrest extends upwardly past the lower support member and is positioned directly below at least a portion of the padded main body, and wherein the armrest, in the deployed position, is configured to extend forwardly away from a front side chest support to support a user's forearm while the user sits on the seat assembly and leans against the chest support surface.

2. The stool of claim 1, wherein the armrest includes a padded base rotatably coupled to the chest support; and a padded member coupled to the padded base and movable from an unexpanded position adjacent the padded base to an extended position so as to move the padded member away from the padded base.

3. The stool of claim 1, further comprising a locking mechanism configured to lock the armrest at a plurality of positions between the stowed locked position and the deployed position.

4. The stool of claim 1, further comprising a locking mechanism assembly having a locked state for holding the armrest stationary relative to the chest support and an unlocked state for allowing movement of the armrest relative to the chest support.

5. The stool of claim 1, wherein the armrest, in the stowed locked position, and the lower support member together define a leg-receiving gap between the chest support and a seat cushion of the seat assembly.

6. The stool of claim 1, further comprising an extension mechanism coupling the armrest to the chest support and configured to allow the armrest to move laterally away from the lower support member independent of rotation of the armrest relative to the chest support.

7. A stool comprising:
a seat assembly;
a chest support including an upper chest support and a lower chest support movable away from one another, wherein the upper chest support extends laterally outward past opposing sides of the lower chest support;
an armrest movable between a locked chest-support position for supporting a user's chest and a locked lowered position for supporting the user's arm while the user straddles the stool, wherein the upper chest support extends laterally outward past a portion of the armrest in the locked chest-support position; and an extension mechanism coupling the armrest to the chest support, wherein the extension mechanism is configured to allow the armrest to move from an undeployed state to a deployed state, wherein the armrest, in the undeployed state, is positioned underneath at least a portion of the chest support, and wherein the armrest, in the deployed state, is positioned subjacent the at least the portion.

8. The stool of claim 7, wherein the chest support includes multiple padded sections movable away from one another such that the multiple sections are spaced apart from one another.

9. A stool comprising:

a seat assembly:

a chest support including a lower chest support and an upper chest support;

an armrest movable between a locked chest-support position for supporting a user's chest and a locked lowered position for supporting the user's arm while the user straddles the stool, wherein the upper chest support extends laterally outward past opposing sides of the lower chest support and a portion of the armrest while the upper chest support is coupled to the lower chest support; and an extension mechanism coupling the armrest to the chest support, wherein the extension mechanism is configured to allow the armrest to move between an undeployed state and a deployed state, wherein the armrest, in the undeployed state, is positioned underneath at least a portion of the chest support, and wherein the armrest, in the deployed state, is positioned subjacent the at least the portion.

10. The stool of claim 9, wherein the extension mechanism is configured to allow the armrest to move laterally outward past the upper chest support.

* * * * *